US012083016B2

(12) United States Patent
Mujwid et al.

(10) Patent No.: US 12,083,016 B2
(45) Date of Patent: Sep. 10, 2024

(54) PUMP ASSEMBLY FOR A PENILE PROSTHESIS

(71) Applicant: Boston Scientific Scimed, Inc., Maple Grove, MN (US)

(72) Inventors: James Ryan Mujwid, Hudson, WI (US); Mark Edward DiLoreto, Chaska, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 95 days.

(21) Appl. No.: 17/450,779

(22) Filed: Oct. 13, 2021

(65) Prior Publication Data
US 2022/0117739 A1    Apr. 21, 2022

Related U.S. Application Data

(60) Provisional application No. 63/198,397, filed on Oct. 15, 2020.

(51) Int. Cl.
*A61F 2/26* (2006.01)
*A61F 2/48* (2006.01)

(52) U.S. Cl.
CPC ............ *A61F 2/26* (2013.01); *A61F 2/484* (2021.08); *A61F 2230/0069* (2013.01); *A61F 2240/001* (2013.01); *A61F 2250/0003* (2013.01); *A61F 2250/0013* (2013.01)

(58) Field of Classification Search
CPC .... A61F 2/26; A61F 2/484; A61F 2230/0069; A61F 2240/001; A61F 2250/0003; A61F 2250/0013
See application file for complete search history.

(56) References Cited

U.S. PATENT DOCUMENTS

| 4,566,446 A | 1/1986 | Fogarty et al. |
| 5,141,509 A | 8/1992 | Burton et al. |
| 6,003,906 A | 12/1999 | Fogarty et al. |
| 6,171,233 B1 | 1/2001 | Willard et al. |

(Continued)

FOREIGN PATENT DOCUMENTS

| EP | 1255513 B1 | 5/2005 |
| EP | 1670393 B1 | 9/2009 |

(Continued)

OTHER PUBLICATIONS

Invitation to Pay Additional Fees for PCT Application No. PCT/US2021/071859, mailed on Jan. 31, 2022, 10 pages.

*Primary Examiner* — Samuel G Gilbert
(74) *Attorney, Agent, or Firm* — Brake Hughes Bellermann LLP

(57) ABSTRACT

An inflatable penile prosthesis may include a fluid reservoir configured to hold fluid, an inflatable member, and a pump assembly configured to transfer fluid between the fluid reservoir and the inflatable member. The pump assembly may include a pump bulb, a valve block, a plurality of valves disposed within the valve block, a first fluid port in fluid communication with the fluid reservoir, and a second fluid port in fluid communication with the inflatable member. The plurality of valves includes a control valve configured to move between an inflation position and a deflation position to control the flow of fluid within the valve block and the transfer of fluid between the fluid reservoir and the inflatable member.

18 Claims, 25 Drawing Sheets

(56) References Cited

U.S. PATENT DOCUMENTS

| | | |
|---|---|---|
| 6,443,887 B1 | 9/2002 | Derus et al. |
| 6,533,719 B2 | 3/2003 | Kuyava et al. |
| 6,558,315 B1 | 5/2003 | Kuyava |
| 6,723,042 B2 | 4/2004 | Almli et al. |
| 6,730,017 B2 | 5/2004 | Kuyava et al. |
| 6,808,489 B2 | 10/2004 | George et al. |
| 6,808,490 B1 | 10/2004 | Ling et al. |
| 6,929,599 B2 | 8/2005 | Westrum |
| 6,935,847 B2 | 8/2005 | Kuyava et al. |
| 6,991,601 B2 | 1/2006 | Kuyava et al. |
| 6,991,604 B2 | 1/2006 | Cantrell |
| 6,997,919 B2 | 2/2006 | Olsen et al. |
| 7,169,103 B2 | 1/2007 | Ling et al. |
| 7,244,227 B2 | 7/2007 | Morningstar et al. |
| 7,250,026 B2 | 7/2007 | Kuyava et al. |
| 7,350,538 B2 | 4/2008 | Kuyava et al. |
| 7,390,296 B2 | 6/2008 | Mische |
| 7,407,482 B2 | 8/2008 | Kuyava et al. |
| 7,438,682 B2 | 10/2008 | Kuyava et al. |
| 7,442,165 B2 | 10/2008 | Forsell |
| 7,637,861 B2 | 12/2009 | Kuyava et al. |
| 7,717,845 B2 | 5/2010 | George et al. |
| 7,874,978 B2 | 1/2011 | Kuyava et al. |
| 7,914,439 B2 | 3/2011 | Kuyava et al. |
| 7,946,975 B2 | 5/2011 | George et al. |
| 7,963,909 B2 | 6/2011 | George et al. |
| 8,016,746 B2 | 9/2011 | Ellering |
| 8,062,209 B2 | 11/2011 | Rowland et al. |
| 8,109,870 B2 | 2/2012 | Kuyava et al. |
| 8,167,788 B2 | 5/2012 | Arp et al. |
| 8,241,203 B2 | 8/2012 | Fogarty |
| 8,257,246 B1 | 9/2012 | Fogarty |
| 8,276,591 B2 | 10/2012 | Henkel et al. |
| 8,337,392 B2 | 12/2012 | Morningstar |
| 8,348,826 B2 | 1/2013 | Gomez-Llorens |
| 8,491,462 B2 | 7/2013 | Chechik |
| 8,517,916 B2 | 8/2013 | Ellering |
| 8,523,761 B2 | 9/2013 | Ellering |
| 8,545,393 B2 | 10/2013 | Ellering |
| 8,568,294 B2 | 10/2013 | Ellering |
| 8,617,052 B2 | 12/2013 | Fogarty |
| 8,632,456 B2 | 1/2014 | Fogarty et al. |
| 8,641,601 B2 | 2/2014 | Ellering |
| 8,684,910 B2 | 4/2014 | Chechik |
| 8,740,769 B2 | 6/2014 | Chechik |
| 8,740,771 B2 | 6/2014 | Ellering |
| 8,801,594 B2 | 8/2014 | Fogarty |
| 8,932,203 B2 | 1/2015 | Ellering |
| 8,932,204 B2 | 1/2015 | Fogarty et al. |
| 8,939,889 B1 | 1/2015 | Chechik |
| 8,939,890 B2 | 1/2015 | Morningstar |
| 8,951,186 B2 | 2/2015 | Ellering |
| D725,271 S | 3/2015 | Chechik |
| 8,974,370 B2 | 3/2015 | Chechik |
| 9,017,245 B2 | 4/2015 | Forsell |
| 9,089,426 B2 | 7/2015 | Henkel et al. |
| 9,101,474 B2 | 8/2015 | Derus |
| 9,186,251 B2 | 11/2015 | Fogarty et al. |
| 9,241,824 B2 | 1/2016 | Ellering |
| 9,308,088 B2 | 4/2016 | Chechik |
| 9,554,937 B2 | 1/2017 | Daniel |
| 9,561,107 B2 | 2/2017 | Daniel |
| 9,566,155 B2 | 2/2017 | Chechik |
| 9,649,217 B2 | 5/2017 | Daniel |
| 9,795,484 B2 | 10/2017 | Daniel |
| 9,814,554 B2 | 11/2017 | Mcclurg |
| 9,861,481 B2 | 1/2018 | Daniel |
| 9,877,834 B2 | 1/2018 | Vaingas et al. |
| 9,907,653 B2 | 3/2018 | Taylor |
| 9,956,079 B2 | 5/2018 | Daniel |
| 9,987,136 B2 | 6/2018 | Daniel |
| 9,999,508 B2 | 6/2018 | Darnell et al. |
| 10,098,741 B2 | 10/2018 | Wolf |
| 10,285,815 B2 | 5/2019 | Henkel et al. |
| 10,327,902 B2 | 6/2019 | Forsell |
| 10,383,730 B2 | 8/2019 | Daniel |
| 10,682,233 B2 | 6/2020 | Wolf |
| 10,722,367 B2 | 7/2020 | Kansas et al. |
| 10,729,547 B2 | 8/2020 | Darnell et al. |
| 11,311,382 B2 | 4/2022 | Mujwid et al. |
| 11,865,002 B2 | 1/2024 | Diloreto et al. |
| 2002/0082471 A1 | 6/2002 | Henkel et al. |
| 2002/0082472 A1* | 6/2002 | Derus ............... A61F 2/26 600/40 |
| 2002/0082473 A1 | 6/2002 | Henkel et al. |
| 2007/0142700 A1 | 6/2007 | Fogarty et al. |
| 2011/0015738 A1* | 1/2011 | Vaingast ............... A61F 2/0036 623/14.13 |
| 2013/0072751 A1 | 3/2013 | Fogarty |
| 2013/0253265 A1 | 9/2013 | Henkel et al. |
| 2014/0259641 A1* | 9/2014 | Brannan ............ A61B 18/1815 29/602.1 |
| 2016/0120649 A1 | 5/2016 | Vaingast et al. |
| 2017/0209271 A1 | 7/2017 | Daniel |
| 2018/0042724 A1 | 2/2018 | Diloreto |
| 2018/0214271 A1 | 8/2018 | Poucher et al. |
| 2018/0214272 A1 | 8/2018 | Elist |
| 2018/0289489 A1 | 10/2018 | Hakky |
| 2019/0000626 A1 | 1/2019 | Tal et al. |
| 2019/0307567 A1 | 10/2019 | Mujwid et al. |
| 2020/0146827 A1 | 5/2020 | Allen et al. |
| 2020/0155319 A1 | 5/2020 | Allen et al. |
| 2020/0163770 A1 | 5/2020 | Mujwid et al. |
| 2022/0211503 A1 | 7/2022 | Mujwid et al. |

FOREIGN PATENT DOCUMENTS

| | | |
|---|---|---|
| EP | 2272465 A1 | 1/2011 |
| EP | 2391302 A1 | 12/2011 |
| EP | 2391307 A1 | 12/2011 |
| EP | 2531144 B1 | 6/2014 |
| EP | 2767261 A1 | 8/2014 |
| EP | 2805689 A1 | 11/2014 |
| EP | 2839809 A1 | 2/2015 |
| EP | 1962745 B1 | 9/2015 |
| EP | 2501339 B1 | 2/2016 |
| EP | 2741712 B1 | 6/2016 |
| EP | 2957263 B1 | 9/2016 |
| EP | 2965719 B1 | 10/2016 |
| EP | 3123981 A1 | 2/2017 |
| EP | 3135250 A1 | 3/2017 |
| EP | 2747710 B1 | 4/2017 |
| EP | 3150175 A1 | 4/2017 |
| EP | 3222249 A1 | 9/2017 |
| EP | 3242631 A1 | 11/2017 |
| EP | 2696808 B1 | 7/2018 |
| EP | 2415422 B1 | 8/2018 |
| EP | 3384875 A1 | 10/2018 |
| EP | 3393402 A1 | 10/2018 |
| EP | 3100702 B1 | 12/2018 |
| EP | 3028673 B1 | 7/2019 |
| EP | 3001980 B1 | 11/2019 |
| EP | 3563807 A1 | 11/2019 |
| EP | 3574870 A1 | 12/2019 |
| KR | 101131148 B1 | 3/2012 |
| WO | 2013020555 A2 | 2/2013 |
| WO | 2014123408 A1 | 8/2014 |
| WO | 2020112443 A1 | 6/2020 |
| WO | 2021029834 A1 | 2/2021 |
| WO | 2021102458 A1 | 5/2021 |

\* cited by examiner

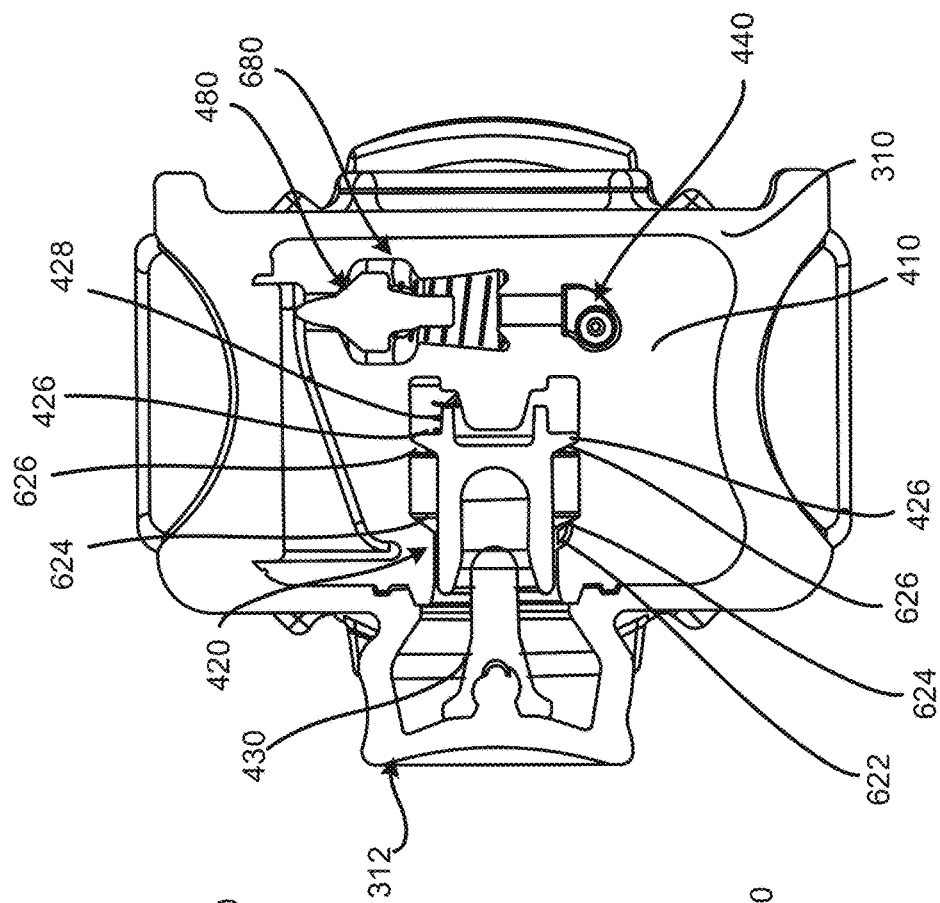
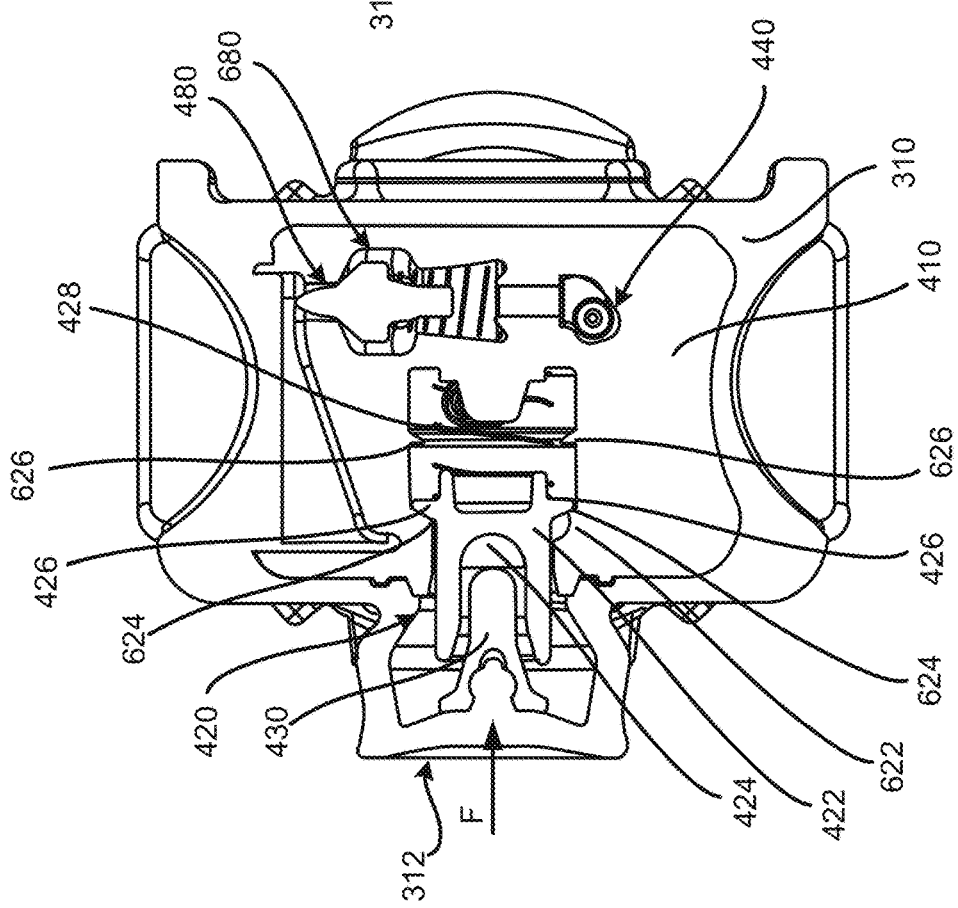

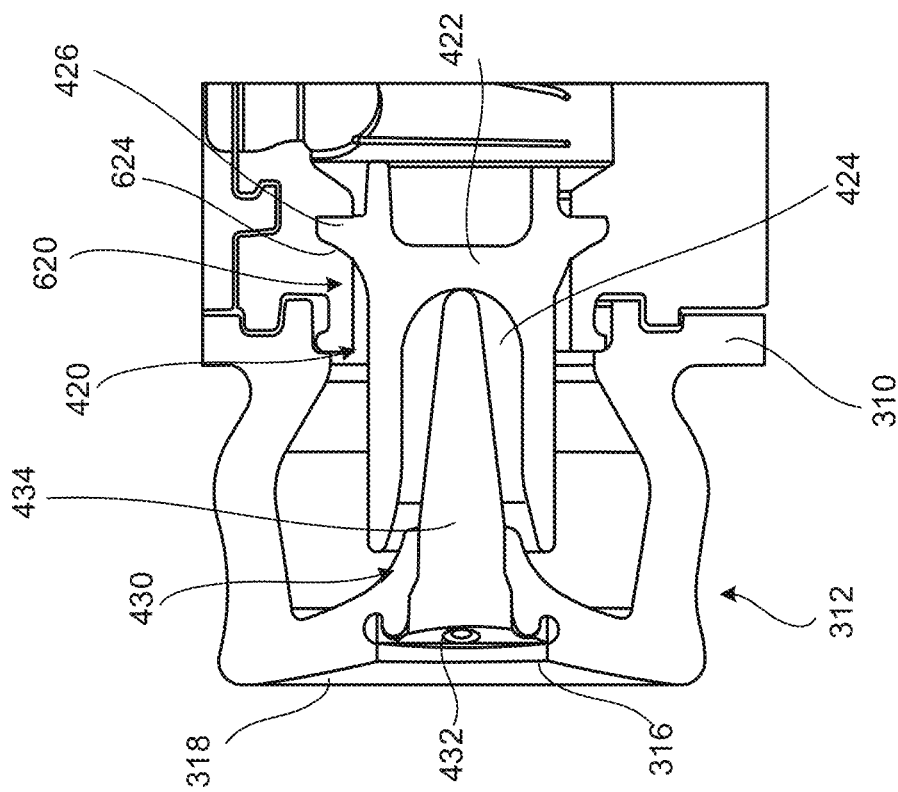
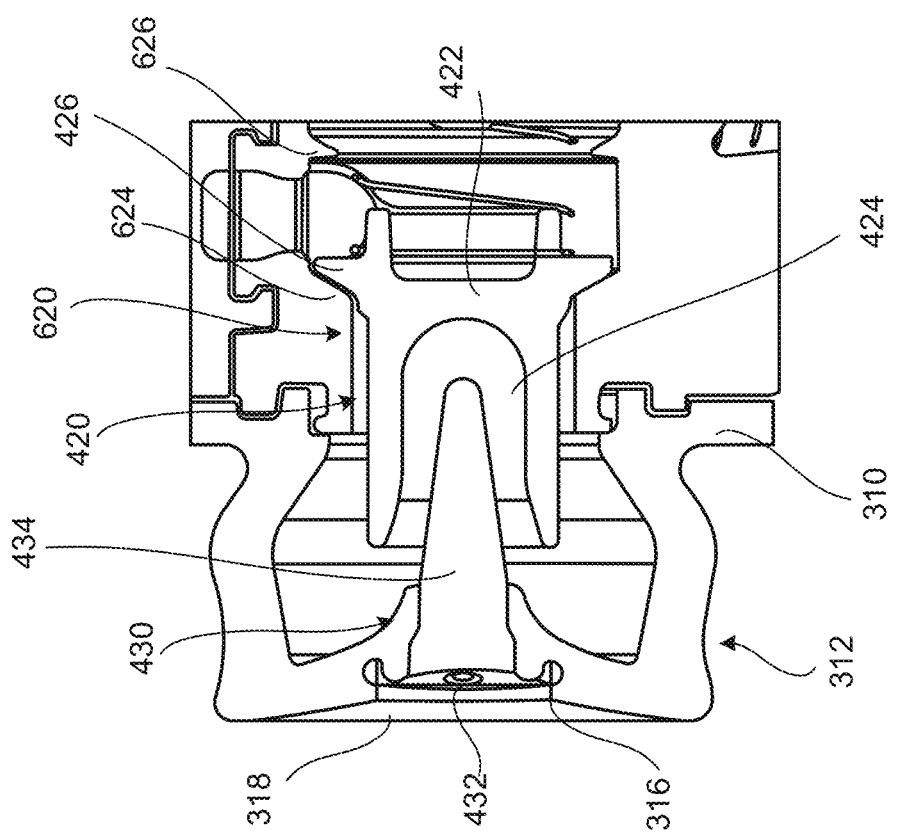
FIG. 14A
FIG. 14B

PUMP ASSEMBLY FOR A PENILE PROSTHESIS

CROSS-REFERENCE TO RELATED APPLICATION

This application claims priority to U.S. Provisional Patent Application No. 63/198,397, filed on Oct. 15, 2020, entitled "PUMP ASSEMBLY FOR A PENILE PROSTHESIS", the disclosure of which is incorporated by reference herein in its entirety.

TECHNICAL FIELD

This disclosure relates generally to bodily implants, and more specifically to bodily implants such as a penile prosthesis that includes a pump.

BACKGROUND

One treatment for male erectile dysfunction is the implantation of a penile prosthesis that mechanically erects the penis. Some existing penile prostheses include inflatable cylinders or members that can be inflated or deflated using a pump mechanism. The pump mechanism transfers fluid between a fluid reservoir and the inflatable members to inflate and deflate the inflatable members. The pump mechanism may include a pump bulb and a valve block, with one or more valve components that control fluid flow through the valve block to provide for the inflating or deflating of the inflatable members. The complexity of the valve components and the arrangement of the valve components in the valve block may disrupt the smooth transfer of fluid between the reservoir and the inflatable members, having an adverse impact on the operation of the prosthesis.

SUMMARY

According to an aspect, an inflatable penile prosthesis includes a fluid reservoir configured to hold fluid, an inflatable member, and a pump assembly configured to transfer the fluid between the fluid reservoir and the inflatable member. The pump assembly may include a valve assembly, including a housing, a valve block received in the housing, and at least one valve positioned within a fluid passageway formed in the valve block and configured to move between an inflation position corresponding to an inflation mode of the pump assembly and a deflation position corresponding to a deflation mode of the pump assembly. The at least one valve may include a first movable member received in the fluid passageway, and a second movable member coupled to the housing and engaged with the first movable member. The pump assembly may also include a pump bulb coupled to a first portion of the valve assembly, and a plurality of fluid ports at a second portion of the valve assembly, including a first port fluidically connected to the fluid reservoir and a second port fluidically connected to the inflatable member.

In some implementations, the at least one valve includes a control valve. The first movable member may include a valve body having a cavity defined therein, a flange extending outward from a first end portion of the valve body, and an opening at a second end portion of the valve body defining an opening into the cavity. The second movable member may include a head portion coupled to the housing, and a shaft portion coupled to the head portion and movably received in the cavity defined in the valve body.

In some implementations, in the deflation position of the control valve, the flange is configured to engage a first lip defined in a wall portion of the fluid passageway. In the inflation position of the control valve, the flange is configured to engage a second lip defined in the wall portion of the fluid passageway. In some implementations, the control valve also includes a biasing member, the biasing member having an end that abuts the flange so as to apply a biasing force that biases the valve body against the first lip in the deflation position, and against the second lip in the inflation position. In some implementations, the control valve is configured to disengage the second lip and engage the first lip in response to an external force applied to the second movable member, to switch from the inflation mode to the deflation mode of the pump assembly.

In some implementations, the inflatable penile prosthesis includes a pressure relief channel defined in the wall portion of the fluid passageway, adjacent to the second lip, wherein the pressure relief channel is configured to shift the flange back into engagement with the second lip in response to a pressure in the fluid passageway that is greater than a threshold pressure.

In some implementations, a length of the shaft portion of the second movable member is greater than a depth of the cavity. In some implementations, the shaft portion is tapered such that a diameter of the shaft portion AT a proximal end portion of the second movable member is greater than a diameter of the shaft portion at a distal end portion of the second movable member. In some implementations, the shaft portion of the second movable member is received through an opening in a portion of the housing defining a button component of the pump assembly, such that the head portion is positioned at an outer side of the housing and the shaft portion is positioned at an interior side of the housing. In some implementations, the head portion of the second movable member is over molded by a material of a portion of the housing defining a button component of the pump assembly to couple the second movable member to the housing.

In some implementations, the at least one valve includes a plurality of valves in the fluid passageway formed in the valve block, the plurality of valves including a refill valve controlling fluid flow from the reservoir to the pump bulb, an inflation valve controlling fluid flow from the pump bulb to the inflatable member, and an anti-auto inflation valve controlling a fluid flow between the inflatable member and the reservoir. In some implementations, the anti-auto inflation valve is a one-way valve that selectively allows a flow of fluid from the inflatable member to the reservoir, bypassing the pump bulb, and that restricts a flow of fluid from the reservoir to the inflatable member. In some implementations, the refill valve includes a refill valve body, a protrusion at an intermediate portion of the refill valve body, and at least one groove formed in an outer peripheral portion of the protrusion on the refill valve body, extending in a flow direction of fluid through refill valve. In some implementations, the inflation valve includes an inflation valve body, a protrusion at an intermediate portion of the refill valve body, at least one groove formed in an outer peripheral portion of the protrusion on the inflation valve body, extending in a flow direction of fluid through inflation valve and a biasing member having an end thereof positioned against the protrusion.

In some implementations, portions of the fluid passageway corresponding to positions of the plurality of valves include fluting to guide flow through the fluid passageway and through the plurality of valves.

In some implementations, the housing includes a first housing, a second housing coupled to the first housing, at least one adhesive port defined in one of the first housing or the second housing, and at least one fill channel defined between mating surfaces of the first housing and the second housing, the at least one fill channel being fluidically connected to the at least one adhesive port such that adhesive injected into the at least one fill channel via the at least one adhesive port couples the first housing and the second housing.

In another general aspect, a method of manufacturing an inflatable penile prosthesis includes providing a valve assembly housing, providing a valve block within the valve assembly housing, the valve block including at least one valve positioned in a fluid passageway defined in the valve block, and coupling a tube adaptor housing to the valve assembly housing. Coupling the tube adaptor housing and the valve assembly housing may include injecting adhesive into at least one adhesive port formed in one of the tube adaptor housing or the valve assembly housing and into a corresponding fill channel defined between mating surfaces of the tube adaptor housing and the valve assembly housing, and adhering the tube adaptor housing to the valve assembly housing.

In some implementations, providing the valve block within the valve assembly housing includes providing a control valve in the fluid passageway formed in the valve block, the control valve including a first movable member and a second movable member. The first movable member may include a valve body having a cavity defined therein, a flange extending outward from a first end portion of the valve body, and an opening at a second end portion of the valve body defining an opening into the cavity. The second movable member may include a head portion coupled to the valve assembly housing, and a shaft portion coupled to the head portion and movably received in the cavity defined in the valve body.

In some implementations, providing the valve assembly housing includes providing a button component at a portion of the valve assembly housing corresponding to the control valve. In some implementations, the method also includes inserting the shaft portion of the second movable member through an opening formed in the button component of the valve assembly housing such that the head portion of the second movable member is positioned on an exterior of the valve assembly housing and the shaft portion is positioned in an interior of the valve assembly housing, and adhering mating surfaces of the head portion of the second movable member and the valve assembly housing to couple the second movable member to the button component of the valve assembly housing.

In some implementations, providing the valve assembly housing includes providing a button component at a portion of the valve assembly housing corresponding to the control valve. In some implementations, the method includes molding the valve assembly housing, including positioning the head portion of the second movable member at a position corresponding to the button component of the valve assembly housing, and over-molding the head portion of the second movable member with material of the valve assembly housing to couple the head portion of the second movable member to the button component of the valve assembly housing. In some implementations, the method also includes attaching the shaft portion of the second movable member to the head portion after the over-molding.

BRIEF DESCRIPTION OF THE DRAWINGS

FIGS. 9A and 9B are cross-sectional views taken along line B-B of FIG. 3A, illustrating movement of a control valve of the example pump assembly in response to an external force.

FIGS. 14A and 14B are cross-sectional views of example first and second movable members of an example control valve of the example pump assembly, according to an aspect.

DETAILED DESCRIPTION

Detailed implementations are disclosed herein. However, it is understood that the disclosed implementations are merely examples, which may be embodied in various forms. Therefore, specific structural and functional details disclosed herein are not to be interpreted as limiting, but merely as a basis for the claims and as a representative basis for teaching one skilled in the art to variously employ the implementations in virtually any appropriately detailed structure. Further, the terms and phrases used herein are not intended to be limiting, but to provide an understandable description of the present disclosure.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the implementations are directed to bodily implants. The term patient or user may hereafter be used for a person who benefits from the medical device or the methods disclosed in the present disclosure. For example, the patient can be a person whose body is implanted with the medical device or the method disclosed for operating the medical device by the present disclosure.

Figure 1:
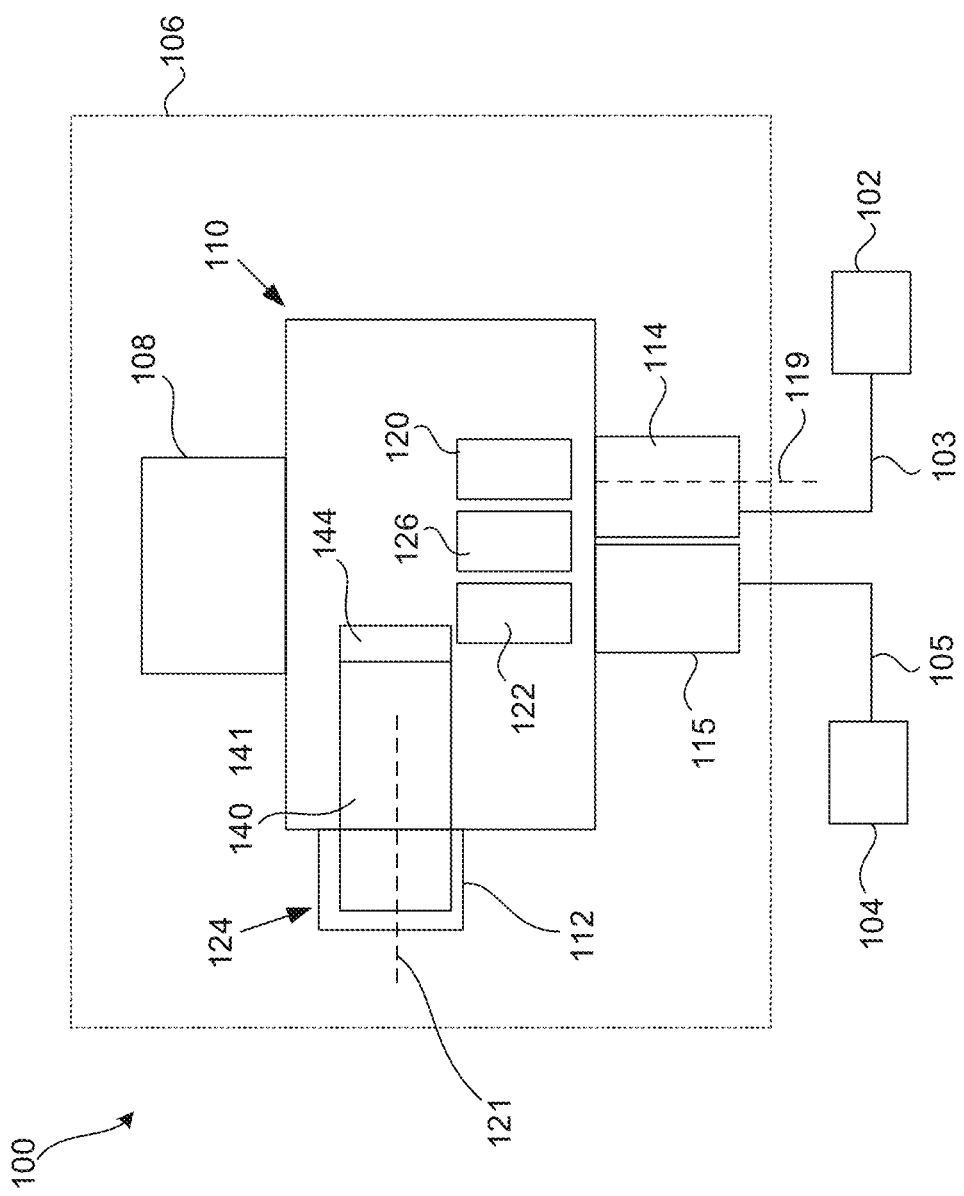
FIG. 1 is a schematic diagram of an inflatable penile prosthesis according to an aspect.

FIG. 1 is a schematic diagram of an example penile prosthesis 100. The example penile prosthesis 100 shown in FIG. 1 includes a fluid reservoir 102, an inflatable member 104, and a pump assembly 106 configured to transfer fluid between the fluid reservoir 102 and the inflatable member 104. The inflatable member 104 may be implanted into the corpus cavernosa of the user, the fluid reservoir 102 may be implanted in the abdomen or pelvic cavity of the user (e.g., the fluid reservoir 102 may be implanted in the lower portion of the abdominal cavity or the upper portion of the pelvic cavity of the user), and the pump assembly 106 may be implanted in the scrotum of the user.

The pump assembly 106 shown in FIG. 1 includes a pump bulb 108, a valve block 110, and a push valve 124 movably coupled to the valve block 110. A first fluid port 114 provides for fluid communication between the fluid reservoir 102 and the valve block 110 via a first conduit connector 103. A second fluid port 115 provides for fluid communication between the inflatable member 104 and the valve block 110 via a second conduit connector 105. The first fluid port 114 and the second fluid port 115 may extend from an end portion of the valve block 110. In some examples, the fluid transfer ports are included in a tube adaptor that is separate from and coupled to the valve block 110. In some examples, the first fluid port 114 includes an elongated tubular member defining a cavity. In some examples, the second fluid port 115 includes two separate elongated tubular members. In an arrangement in which the second fluid port 115 includes two separate elongated tubular members, one tubular member may be fluidically coupled to a first cylinder member of the inflatable member 104 and another tubular member may be fluidically coupled to a second cylinder member of the inflatable member 104.

The push valve 124 is configured to move from an inflation position to a deflation position along an axis 121 within a bore of the valve block 110 in response to being pressed by a user in order to control the direction of the flow of fluid through fluid passageways defined in the valve block 110. In some examples, push valve 124 includes a movable valve element 140 and a biasing member 144 that biases the movable valve element 140 to the inflation position. In some examples, the movable valve element 140 is configured to move to the deflation position in a linear direction in response to a force exerted on the movable valve element 140, such as, for example, a push of the movable valve element 140 by a user. In some examples, the force is a single instantaneous push. In some examples, the force is a sustained force. The pump assembly 106 includes a button component 112 that encloses at least a portion of the movable valve element 140. The button component 112 may be a flexible button-shaped material that extends over the movable valve element 140. In some examples, the button component 112 is defined by a portion of a casing, or a housing, in which the valve block 110 is received. For example, the button component 112 may be integrally formed with the housing of the valve block 110.

The push valve 124 including the movable valve element 140 may be movable between a first position and a second position. The first position of the movable valve element 140 may correspond to an inflation position, in which the inflatable penile prosthesis 100 is in an inflation mode (or an inflation cycle). The second position of the movable valve element 140 may correspond to a deflation position, in which the inflatable penile prosthesis 100 is in a deflation mode (or a deflation cycle). In some examples, a single, instantaneous push of the movable valve element 140 transfers the inflatable penile prosthesis 100 to the deflation position (e.g., as opposed to pressing and holding the movable valve element 140 for a predetermined period of time time). In some examples, movement of the movable valve element 140 to the deflation position causes a fluid pathway to open between the second fluid port 115 and the first fluid port 114 such that fluid can be transferred from the inflatable member 104 to the fluid reservoir 102 via the pump assembly 106 in a manner that bypasses the pump bulb 108.

In contrast, in the inflation mode, the pump bulb 108 is used to transfer fluid from the fluid reservoir 102 to the inflatable member 104. For example, the user may depress (or squeeze) the pump bulb 108 and then release the pump bulb 108. The depression or squeezing of the pump bulb 108 in this manner may be repeated until the desired rigidity is achieved in the inflatable member 104. The release of the depression of the pump bulb 108 generates a suction force that draws fluid from the fluid reservoir 102 to the pump bulb 108. Subsequent depression of the pump bulb 108 expels the fluid from the pump bulb 108 to the inflatable member 104.

The pump bulb 108 may be a flexible member defining an interior cavity. The pump bulb 108 is coupled to and extends from the valve block 110. In some examples, the pump bulb 108 extends from the valve block 110 in a direction that is substantially opposite to the direction in which the first fluid port 114 and the second fluid port 115 extend from the valve block 110. That is, in some examples, the pump bulb 108 and the first and second fluid ports 114, 115 are located on opposite ends of the valve block 110. The pump bulb 108 may be a squeeze pump. In some examples, the pump bulb 108 includes ribbing and/or recessed areas defined on an outer surface thereof, to aid the user in gripping the pump bulb 108. In some examples, the ribbing and/or recessed areas defined on the outer surface of the pump bulb 108 are sized and positioned to define gripping areas that guide finger and/or thumb placement on the pump bulb 108. Sizing and/or positioning of the ribbing and/or recessed areas on the pump bulb 108 may provide indexing for gripping of the pump bulb 108, and may provide for stability as squeezing pressure is applied to and released from the pump bulb 108 by the user. As indicated above, the pump bulb 108 may use suction and pressure to move the fluid into and out of the interior cavity of the pump bulb 108 in the inflation mode. For example, the user may depress or squeeze the pump bulb 108 to expel the fluid out of the cavity. When the flexible member defined by the pump bulb 108 returns to its original shape (i.e., the shape of the pump bulb 108 before depression or squeezing), the resulting suction force draws fluid into the cavity of the pump bulb 108 from the reservoir 102. In some examples, the pump bulb 108 may have a bulb spring rate that is designed to refill the pump bulb 108 in a selected time frame.

One or more fluid passageways are defined through the valve block 110. Valve components disposed within the fluid passageways defined in the valve block 110 control the flow of the fluid through the valve block 110 in the inflation mode and the deflation mode. In some examples, the valve block 110 includes a block of material, with the fluid passageways defined in the block of material and the valve components enclosed in the block of material. In some examples, the valve block 110 includes a silicone material. In some examples, the valve block 110 may be molded from a silicone material having a medium durometer value. In some examples, the pump assembly 106 includes a housing that is disposed over the valve block 110. In some examples the housing forms some or all of the pump bulb 108. In some examples, the housing includes a material (e.g., a polymer material) that is different from the material of the valve block 110. In some examples, the housing includes one or more tactile features that help the user locate the valve block 110. In some examples, tactile features provided on the outer protective casing are sized and/or shaped and/or located to provide for indexing of the valve block 110, so that the fingers and/or thumb of the user are more easily accommodated, and so that the button component 112 of the push valve 124 is more easily located. In some examples, the tactile features include protruded portions, ridges, grooves, bumps, and/or depressions.

The valve block 110 shown in FIG. 1 includes a refill valve 120, an inflation valve 122, and an anti-auto inflation valve 126. The refill valve 120 may be used when the pump bulb 108 is refilled. For example, the refill valve 120 may be in an opened state that allows for fluid flow into the pump bulb 108. The refill valve 120 is not used in the deflation mode. For example, the refill valve 120 may be in a closed state the deflation mode, to restrict the flow of fluid into the pump bulb 108. In some examples, the refill valve 120 is a one-way valve. In some examples, the refill valve 120 is disposed in a fluid passageway within the valve block 110 between the first fluid port 114 and the pump bulb 108. In some examples, the fluid passageway having the refill valve 120 that extends between the first fluid port 114 and the pump bulb 108 is used only for refilling the pump bulb 108, for example, a separated or dedicated fluid pathway. This may decrease bulb refill time (e.g., may decrease the wait time between squeezes). In some examples, the refill valve 120 is fluidically coupled to the bore (the bore in the valve block 110, in which the push valve 124 moves) and the pump bulb 108.

In some examples, the refill valve 120 is aligned with the first fluid port 114. For example, the refill valve 120 may have an inlet and an outlet. Fluid may flow from the first fluid port 114 and into the refill valve 120 through the inlet, through the refill valve 120, and exit the refill valve through the outlet to the pump bulb 108. The first fluid port 114 may define a longitudinal axis 119 that extends along the fluid pathway (e.g., between the inlet and the outlet) of the refill valve 120. In some examples, the longitudinal axis 119 is orthogonal to the axis 121 of the bore in which the push valve 124 is received. The alignment of the refill valve 120 with the first fluid port 114 may minimize fluid pathway tortuosity, and/or decrease pressure drop across the refill valve 120. In some examples, the refill valve 120 includes fluting. The fluting may increase or maximize fluid velocity across the refill valve 120. In some examples, the refill valve 120 includes a biasing member that biases the refill valve 120 to a sealing position. In some examples, the biasing member includes a spring.

The inflation valve 122 may be disposed within a fluid passageway between the pump bulb 108 and the push valve 124. The inflation valve 122 may be used during the inflation of the inflatable member 104 (e.g., when the fluid is transferred from the pump bulb 108 to the inflatable member 104). For example, the inflation valve 122 may be in an open state during the transfer of fluid from the pump bulb 108 to the inflatable member 104. The inflation valve 122 is not used during the deflation mode. For example, the inflation valve 122 may be in a closed state in the deflation mode. In some examples, the inflation valve 122 is a one-way valve including a valve member and a biasing member. The biasing member may bias the valve member to a sealing position. In some examples, the biasing member includes a spring.

In some examples, the anti-auto inflation valve 126 is disposed within a fluid passageway in the valve block 110, to selectively open a passageway between the fluid reservoir 102 and the inflatable member 104. The anti-auto inflation valve 126 allows fluid to flow from the inflatable member 104 back to the reservoir 102, bypassing the pump bulb 108, when the pump assembly 106 is in the deflation mode. In some examples, the anti-auto inflation valve 126 is a one-way valve, such that the anti-auto inflation valve 126 may prevent fluid from flowing from the reservoir 102 to the inflatable member 104 when the pump assembly 106 is in the deflation mode. In some examples, the anti-auto inflation valve 126 includes a valve member and a biasing member. The biasing member may bias the valve member to a sealing position.

In the inflation mode, in response to user manipulation of the pump bulb 108, the fluid may flow from the fluid reservoir, through the first fluid port 114 and into to the pump bulb 108 via the refill valve 120, and then from the pump bulb 108 to the second fluid port 115 via the inflation valve 122 and the push valve 124 and into the inflatable member 104. In response to the movable valve element 140 being pressed to the deflation position, the position in the movable valve element 140 within the bore of the valve block 110 may open a fluid passageway in the valve block 110 to transfer fluid from the inflatable member 104 to the fluid reservoir 102, bypassing the pump bulb 108. For example, the movable valve element 140, when moved to the deflation position, is configured to alter the fluid passageway through the bore to transfer fluid from the second fluid port 115 to the first fluid port 114 such that the pump bulb 108 is bypassed. In some examples, pressure in the internal cavity of the inflatable member 104 may cause some of the fluid to be automatically transferred from the inflatable member 104 to the fluid reservoir 102 via the pump assembly 106, and then the user may squeeze the inflatable member 104 to transfer some of the remaining fluid in the inflatable member 104.

Each of the first conduit connector 103 and the second conduit connector 105 may define at least one lumen configured to transfer the fluid to and from the pump assembly 106. The first conduit connector 103 may be coupled to the pump assembly 106 and the fluid reservoir 102 such that fluid can be transferred between the pump assembly 106 and the fluid reservoir 102 via the first conduit connector 103. For example, the first conduit connector 103 may define a first lumen configured to transfer fluid between the pump assembly 106 and the fluid reservoir 102. The first conduit connector 103 may include a single tube member or multiple tube members for transferring the fluid between the pump assembly 106 and the fluid reservoir 102.

The second conduit connector 105 may be coupled to the pump assembly 106 and the inflatable member 104 such that fluid can be transferred between the pump assembly 106 and the inflatable member 104 via the second conduit connector 105. For example, the second conduit connector 105 may define a second lumen configured to transfer fluid between the pump assembly 106 and the inflatable member 104. The second conduit connector 105 may include a single tube member or multiple tube members for transferring the fluid between the pump assembly 106 and the inflatable member 104. In some examples, the first conduit connector 103 and the second conduit connector 105 may include a silicone rubber material. In some examples, the pump assembly 106 may be directly connected to the fluid reservoir 102.

The inflatable member 104 may be configured to expand in response to the injection of fluid into an internal cavity of the inflatable member 104. For example, in response to injection of the fluid into the inflatable member 104, a length and/or a width of the inflatable member 104 may increase, and a rigidity of the inflatable member 104 may increase. In some examples, the inflatable member 104 may include a pair of inflatable cylinders or at least two cylinders, e.g., a first cylinder member and a second cylinder member. The volumetric capacity of the inflatable member 104 may depend on the size of the inflatable cylinders. In some examples, the volumetric capacity of each cylinder member may vary from about 10 milliliters in smaller cylinder members to about 50 milliliters in larger cylinder members. In some examples, the volumetric capacity of one or more of the cylinder members may be less than 10 milliliters. In some examples, the volumetric capacity of one or more of the cylinder members may be greater than 50 milliliters. In some examples, the first cylinder member may be larger than the second cylinder member. In other examples, a size of the first cylinder member may be the same as a size of the second cylinder member.

The fluid reservoir 102 may include a container having an internal chamber configured to hold or house fluid that is transferred through the pump assembly 106 to inflate the inflatable member 104. The volumetric capacity of the fluid reservoir 102 may vary depending on the size of the inflatable penile prosthesis 100. In some examples, the volumetric capacity of the fluid reservoir 102 may be 3 cubic centimeters to 150 cubic centimeters. In some examples, the fluid reservoir 102 is constructed from the same material as the inflatable member 104. In other examples, the fluid reservoir 102 is constructed from a different material than the inflatable member 104. In some examples, the fluid reservoir 102 has a larger volumetric capacity than the inflatable member 104.

Figure 2:
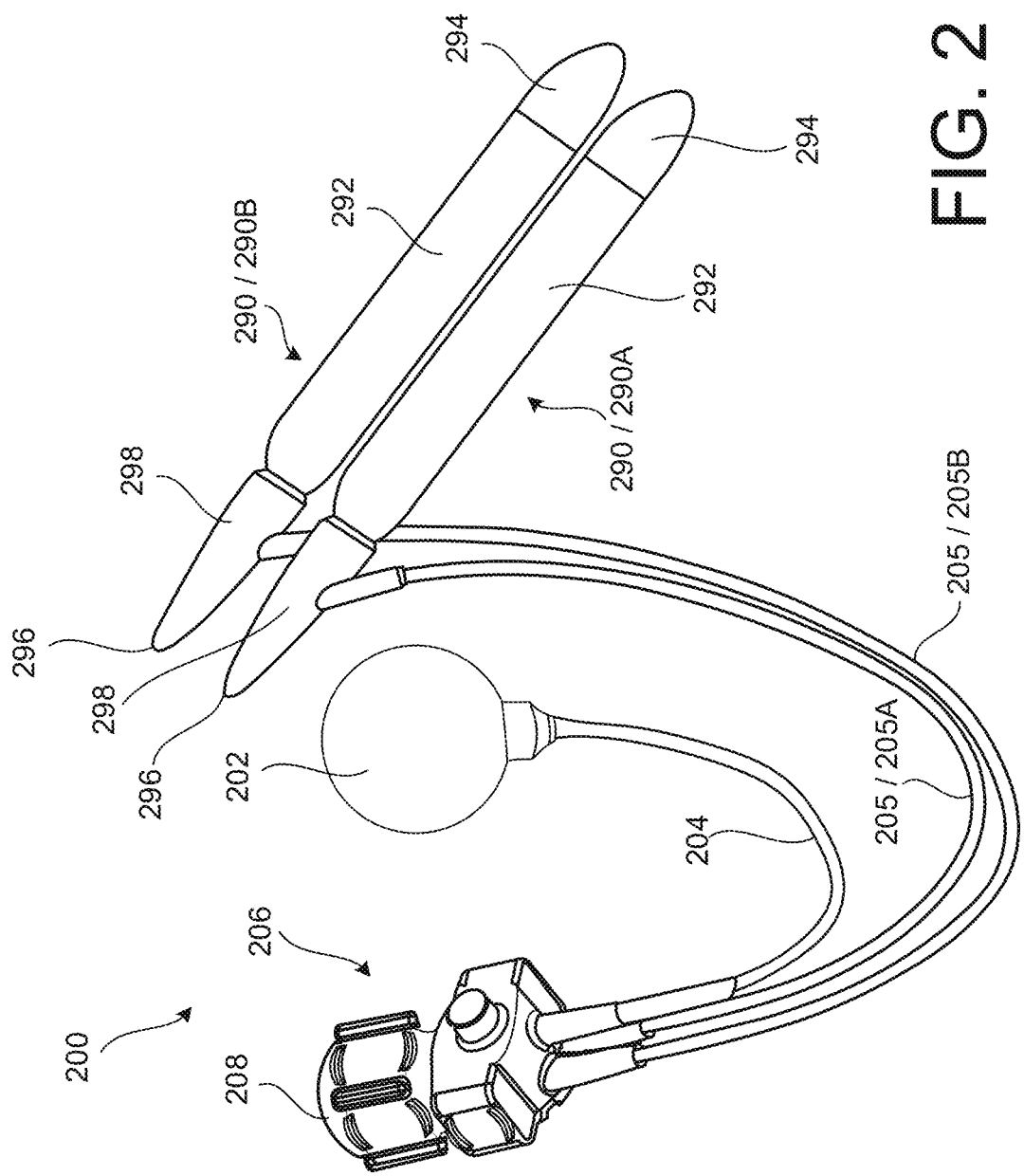
FIG. 2 illustrates an inflatable penile prosthesis according to an aspect.

FIG. 2 illustrates an inflatable penile prosthesis 200 having a pump assembly 206 according to an aspect. The pump assembly 206 may include any of the features of the pump assemblies described with reference to the previous figure(s) included herein, and/or to be described with subsequent figures included herein. The penile prosthesis 200 includes an inflatable member 290 connected to the pump assembly 206. In the example arrangement shown in FIG. 2 the inflatable member 290 includes a pair of inflatable cylinders 290 including a first inflatable cylinder 290A and a second inflatable cylinder 290B. The inflatable cylinders 290 are configured to be implanted in a penis. For example, the first inflatable cylinder 290A may be disposed on a first side of the penis, and the second inflatable cylinder 290B may be disposed on a second side of the penis. Each inflatable cylinder 290 may include a first end portion 294, a cavity or inflation chamber 292, and a second end portion 298 having a rear tip 296.

The pump assembly 206 may be implanted into the scrotum of the patient. Conduit connectors 205, for example a pair of conduit connectors 205 including a first conduit connector 205A and a second conduit connector 205B, may attach the pump assembly 206 to the inflatable cylinders 290 (290A, 290B) such that the pump assembly 206 is in fluid communication with the inflatable cylinders 290. The pump assembly 206 may be in fluid communication with a fluid reservoir 202 via a conduit connector 204. The fluid reservoir 202 may be implanted into the abdomen of the patient. The inflation chamber 292 of each inflatable cylinder 290 may be disposed within the penis. The first end portion 294 of each inflatable cylinder 290 may be at least partially disposed within the crown portion of the penis. The second end portion 298 may be implanted into the patient's pubic region, with the rear tip 296 proximate the pubic bone.

In order to implant the inflatable cylinders 290, the surgeon first prepares the patient. The surgeon may make an incision in the penoscrotal region, e.g., where the base of the penis meets with the top of the scrotum. From the penoscrotal incision, the surgeon may dilate the patient's corpus cavernosa to prepare the patient to receive the inflatable cylinders 290. The corpus cavernosum is one of two parallel columns of erectile tissue forming the dorsal part of the body of the penis, e.g., two slender columns that extend substantially the length of the penis. The surgeon may dilate two regions of the pubic area to prepare the patient to receive the second end portion 298. The surgeon may measure the length of the corpora cavernosa from the incision and the dilated region of the pubic area to determine an appropriate size of the inflatable cylinders 290 to implant.

After the patient is prepared, the penile prosthesis 200 is implanted into the patient. The tip of the first end portion 294 of each inflatable cylinder 290 may be attached to a suture. The other end of the suture may be attached to a needle member (e.g., a Keith needle). The needle member is inserted into the incision and into the dilated corpus cavernosum. The needle member is then forced through the crown of the penis. The surgeon tugs on the suture to pull the inflatable cylinder 290 into the corpus cavernosum. This process is repeated for each inflatable cylinder 290. Once the inflation chamber 292 of each inflatable cylinder 290 is in place, the surgeon may remove the suture from the tip. The surgeon then inserts the second end portion 298 of each inflatable cylinder 290 into the incision and forces the second end portion 298 toward the pubic bone until each inflatable cylinder 290 is in place.

A pump bulb 208 of the pump assembly 206 may be squeezed or depressed by the user in order to facilitate the transfer of fluid from the fluid reservoir 202 to the inflatable cylinders 290. For example, in the inflation mode, in response to user operation of the pump bulb 208, fluid may be drawn from the fluid reservoir 202, through the conduit connector 204 and the pump assembly 206 and into the pump bulb 208, and then output from the pump bulb 208, through the pump assembly 206 and the conduit connectors 205 to the inflatable cylinders 290. In response to a switching to the deflation mode, at least some of the fluid may automatically flow back to the fluid reservoir 202 due to a pressure differential between the inflatable cylinders 290 and the fluid reservoir 202.

Figure 3A:
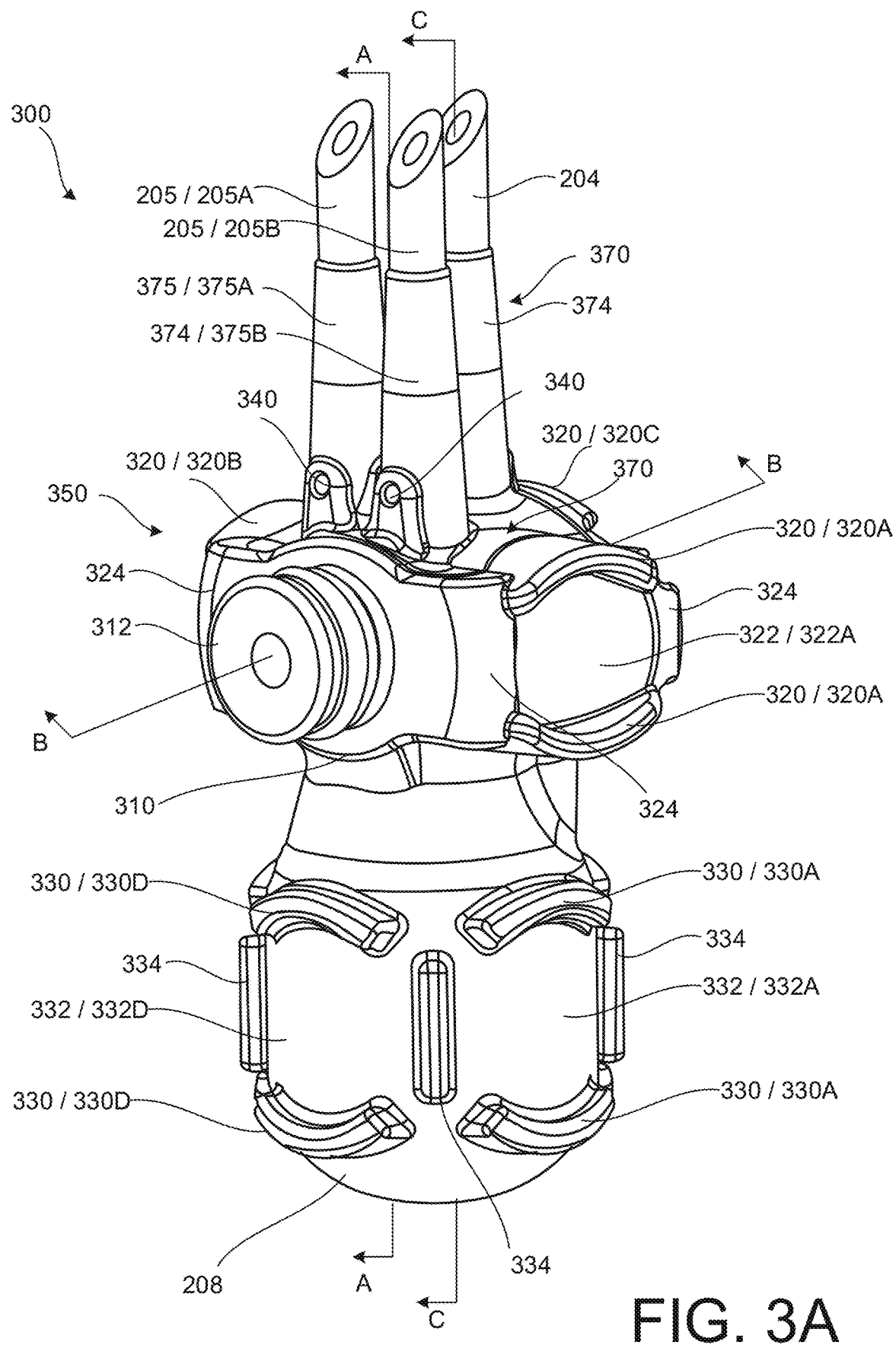
FIGS. 3A and 3B are perspective views of an example pump assembly of an inflatable penile prosthesis according to an aspect.
Figure 3B:
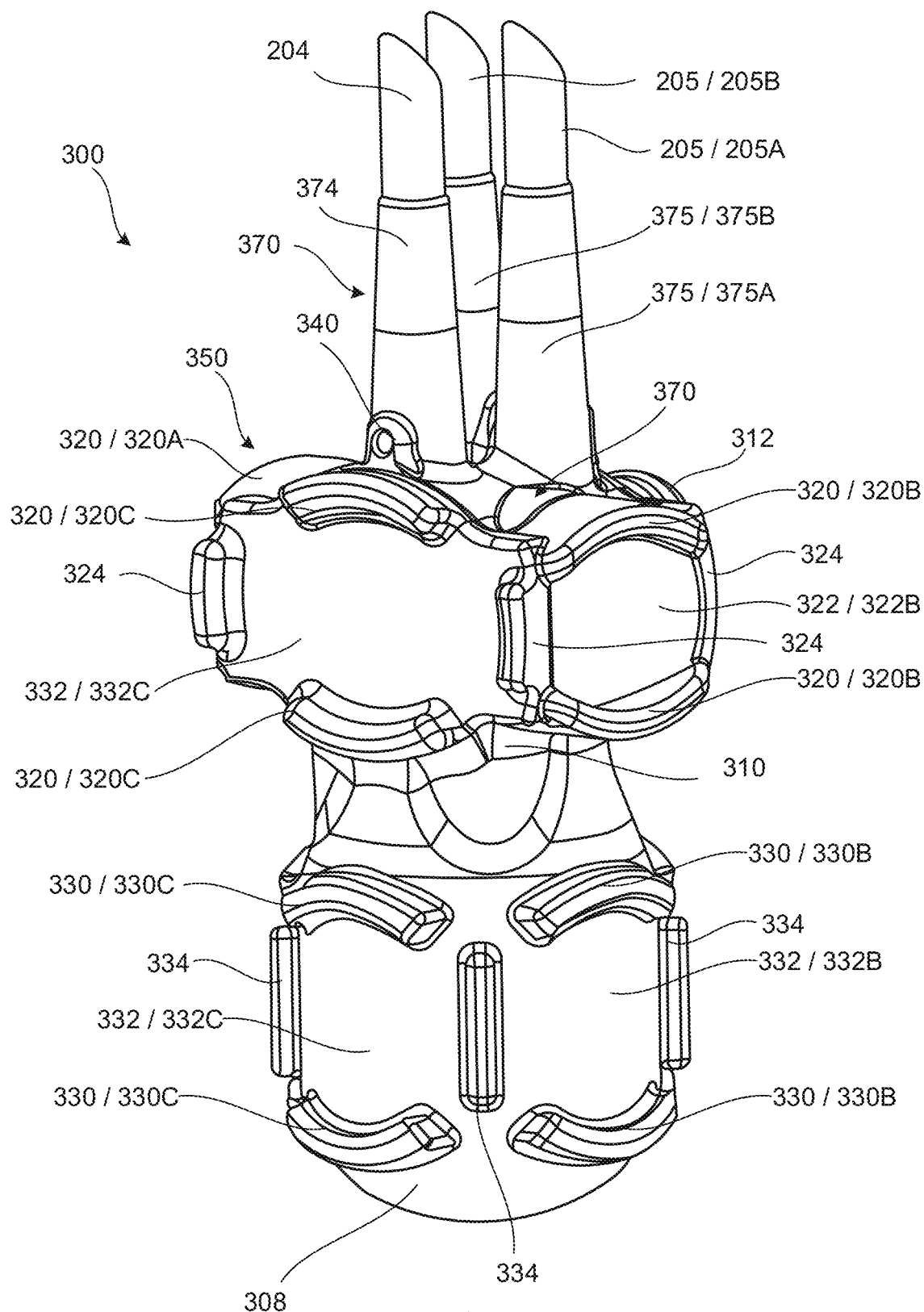
Figure 4A:
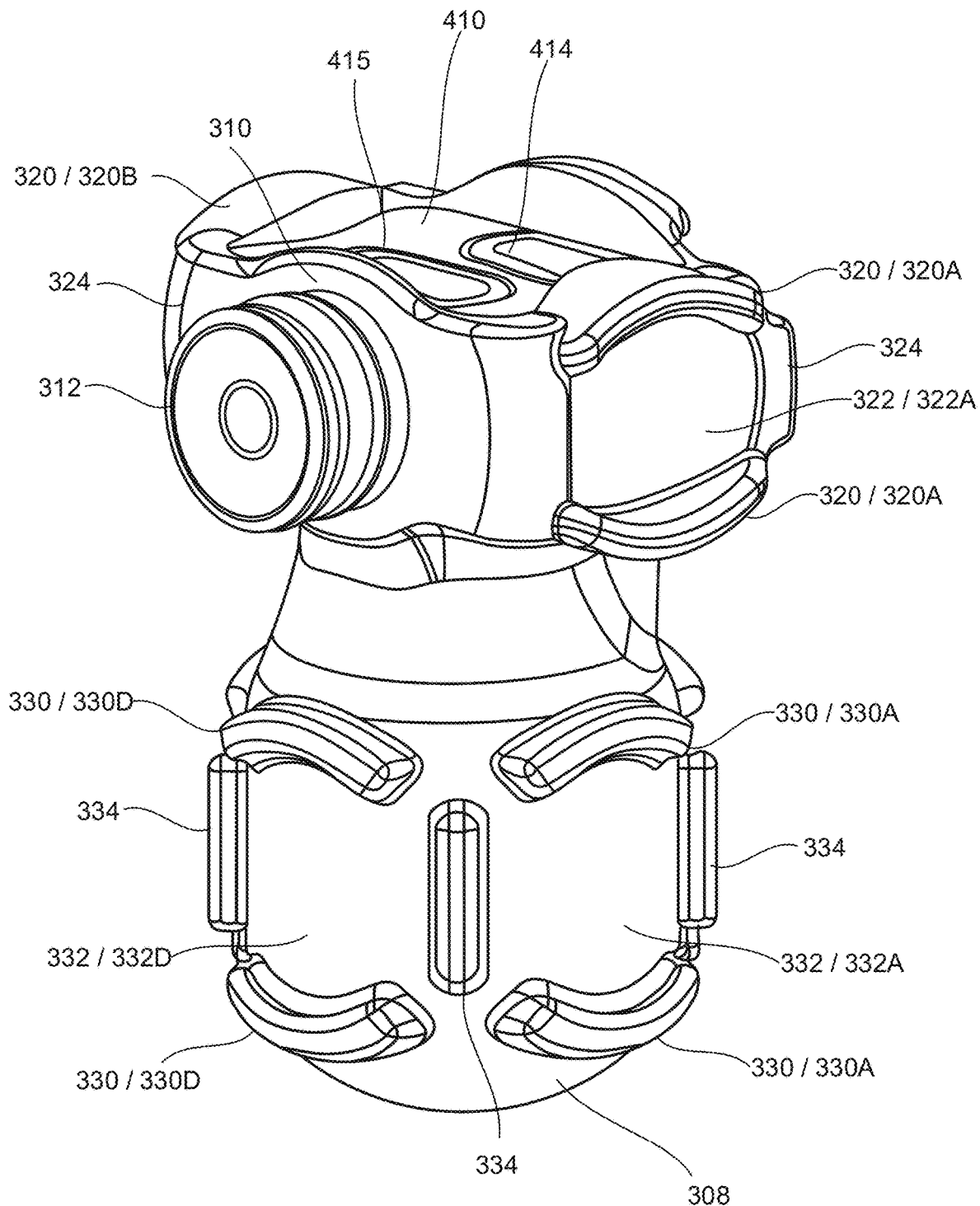
FIG. 4A is a perspective view of an example valve assembly and pump bulb of the example pump assembly shown in FIGS. 3A and 3B.
Figure 4B:
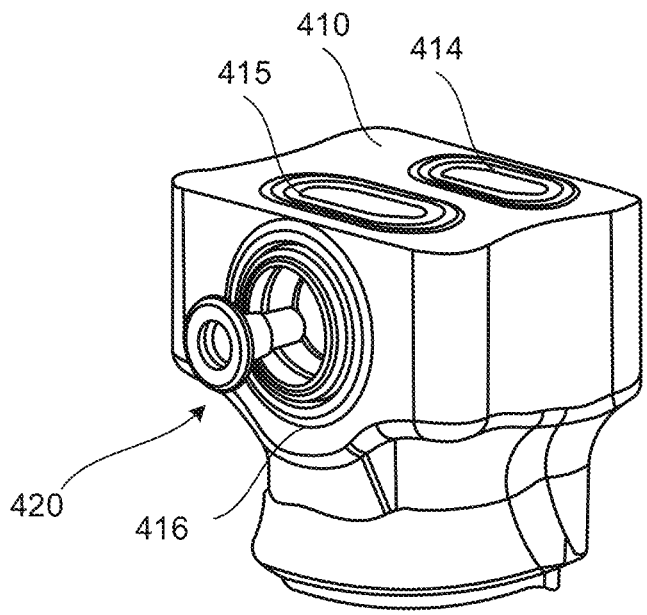
FIG. 4B is an assembled perspective view and FIG. 4C is an exploded perspective view of the example valve assembly shown in FIG. 4A.

FIGS. 3A and 3B are perspective views of an example pump assembly 300 for a penile prosthesis, such as the example penile prosthesis described above and shown in FIG. 2. FIG. 3A is taken from a fist side of the pump assembly 300, and FIG. 3B is taken from a second side of the pump assembly 300. FIG. 4A is a perspective view of the example pump assembly 300 shown in FIGS. 3A and 3B, with a tube adaptor housing 370 removed so that a valve block 410 received in a valve assembly housing 310 is visible. FIG. 4B is an assembled perspective view, and 4C is an exploded perspective view, of the valve block 410 and example valve components of the valve assembly 350, with the valve assembly housing 310 removed.

Figure 5B:
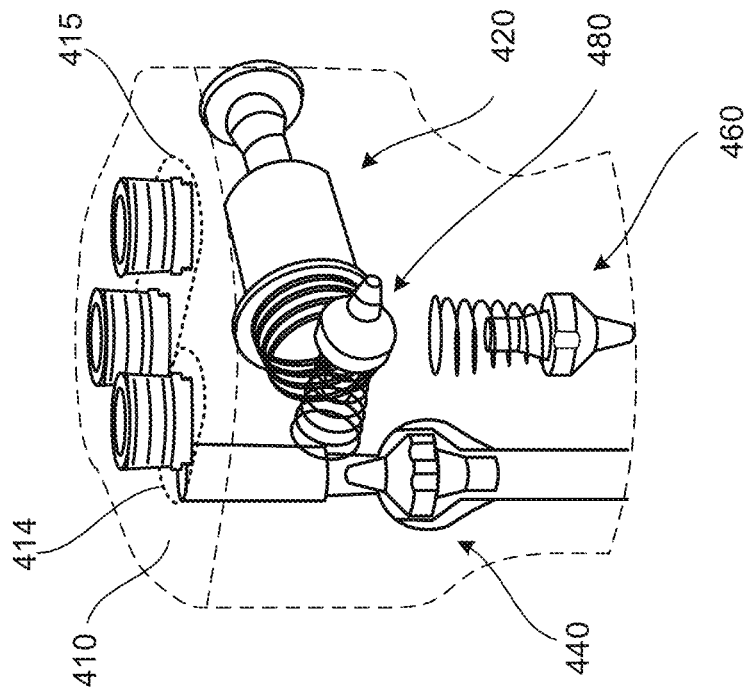
FIGS. 5A and 5B illustrate an example arrangement of valve components in the example valve assembly shown in FIGS. 4B and 4C.
Figure 5A:
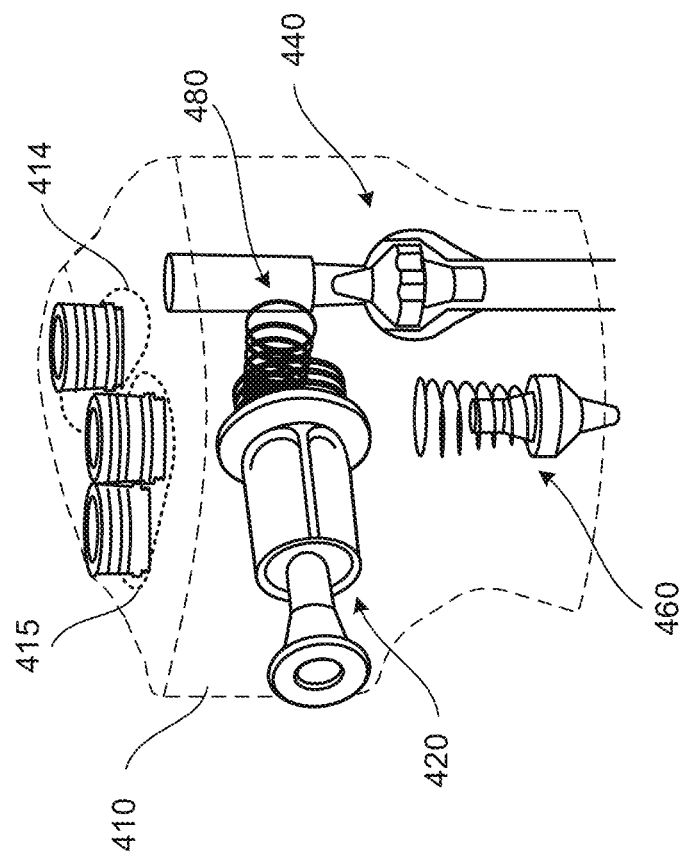

FIGS. 5A and 5B are perspective views taken from the first side and the second side, respectively, of the pump assembly 300, with the housing 310 of the valve assembly 350 removed and the valve block 410 shown in shadow, to illustrate the relative positioning of valve components within the valve block 410.

Figure 6A:
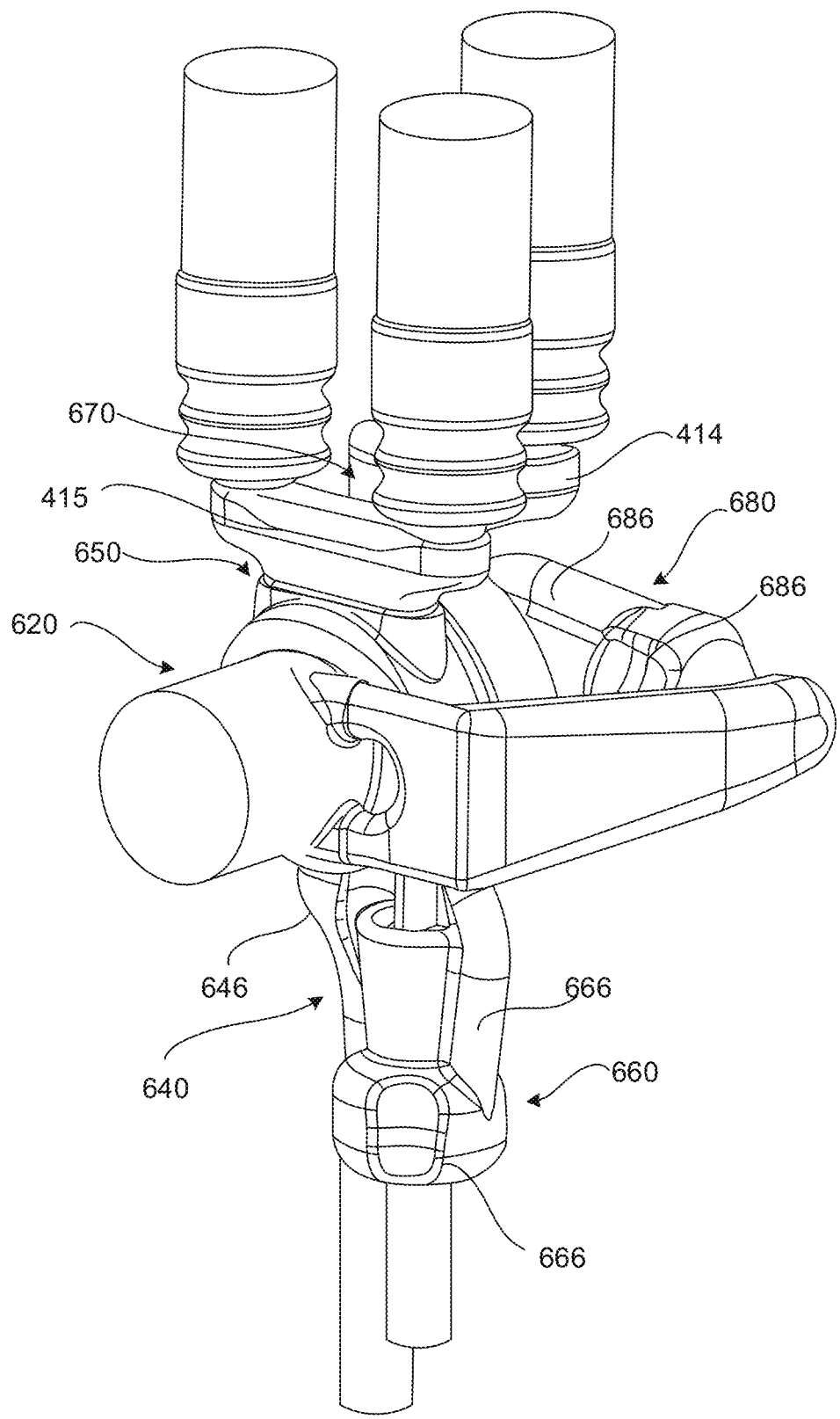
FIGS. 6A and 6B are perspective views illustrating example fluid passageways in the pump assembly shown in FIGS. 3A and 3B.
Figure 6B:
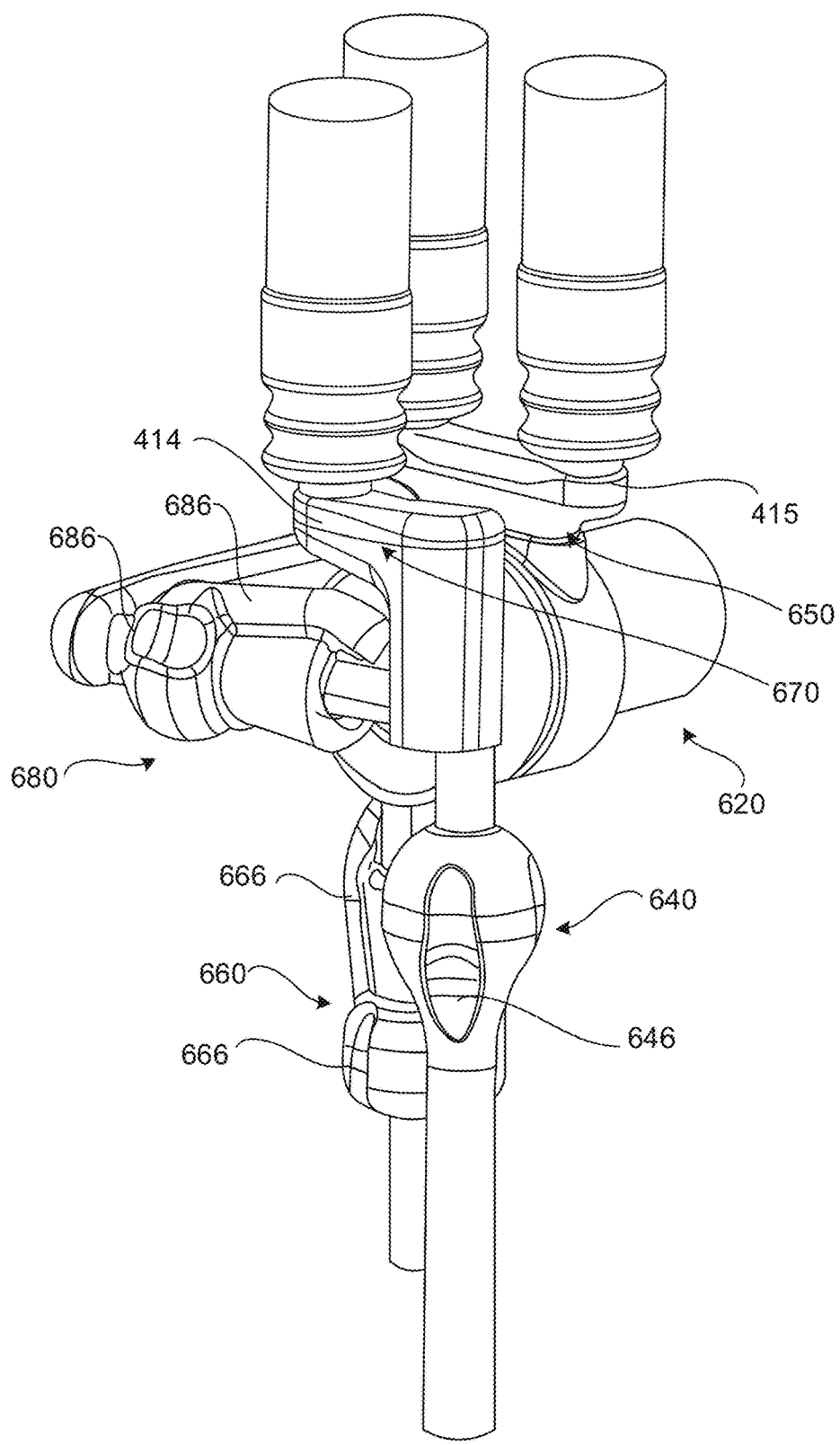

FIGS. 6A and 6B are schematic illustrations of fluid passageways defined in the valve assembly 350. FIG. 6A is taken from the first side of the pump assembly 300, and FIG. 6B is taken from the second side of the pump assembly 300.

The pump assembly 300 includes a valve assembly 350. In some examples, the valve assembly 350 includes a valve assembly housing 310 which components of the valve assembly 350 are received. In some examples, a tube adaptor housing 370 is coupled a first portion of the valve assembly housing 310. The tube adaptor housing 370 may include a plurality of connection ports 374, 375, to facilitate the coupling of the valve assembly 350 to the conduit connectors 204, 205 and the cylinders 290 connected thereto. In some examples, a pump bulb 308 is coupled to a second portion of the valve assembly 350.

In the illustrated example, a first fluid port 414 of the valve block 410 (see FIGS. 4A-4C) is in fluid communication with the first conduit connector 204 via the first connection port 374 of the tube adaptor housing 370, and a second fluid port 415 of the valve block 410 (see FIGS. 4A-4C) is in fluid communication with a pair of second conduit connectors 205 (205A, 205B) via the second connection ports 375 (375A, 375B) of the tube adaptor housing 370. The second fluid port 415 can be connected to more, or fewer conduit connectors than shown. Components of the valve assembly 350 may be received in a valve assembly housing 310. The tube adaptor housing 370 may be coupled to the valve assembly housing 310, to enclose the coupling of the fluid ports 414, 415 and the conduit connectors 204, 205 via the connection ports 374, 375. A button component 312 may be formed at an outer portion of the valve assembly housing 310, at a position corresponding to a control valve 420 (see FIGS. 4A-4C) of the valve assembly 350.

In some examples, the pump assembly 300 includes one or more adhesive ports 340. In some examples, the adhesive ports 340 provide access to fill channels 345 (see FIGS. 7A and 8A) defined between mating surfaces of the valve assembly housing 310 and the tube adaptor housing 370. Adhesive may be injected into the fill channels 345 through the adhesive ports 340. Adhesive filled in the fill channels 345 may provide for the coupling of the valve assembly housing 310 and the tube adaptor housing 370, and may enhance integrity of the coupling of the valve assembly housing 310 and the tube adaptor housing 370.

In some examples, a plurality of ribs 320 is defined on the outer surface of the housing 310 of the valve assembly 350. Recesses 322 defining gripping areas may be formed between sets of ribs 320 on the valve assembly housing 310. For example, a first recess 322A defining a first gripping area may be formed between a first pair of first ribs 320A on a first portion of the housing 310. A second recess 322B defining a second gripping area may be formed between a second set of first ribs 320B on a second portion of the housing 310. A third recess 322C defining a third gripping area may be formed between a third pair of first ribs 320C on a third portion of the housing 310. The button component 312 may be positioned on a fourth portion of the housing 310, between the first and third portions of the housing 310. In some examples, the recesses 322 may be further defined by second ribs 324 positioned between adjacent recesses 322 and adjacent pairs of first ribs 320, so as to separate the adjacent recesses 322 and further delineate the gripping areas. The placement of the ribs 320, 324 and the recesses 322 defining the gripping areas in this manner may provide for indexing on the housing 310 of the valve assembly 350, to assist in location of the button component 312. The placement of the ribs 320, 324 and the recesses 322 defining the gripping areas in this manner may provide for stability in the griping of the pump assembly 300 for manipulation of the button component 312.

In the example shown in FIGS. 3A and 3B, the first ribs 320 on the housing 310 of the valve assembly 350 have a curved shape, such that corresponding peripheral portions of the recesses 322 defining the gripping areas have a corresponding curved contour. The curved contour of the recesses 322 defining the gripping areas on the housing 310 of the valve assembly 350 may further result in gripping areas having a shape that accommodates finger and/or thumb placement, thus further enhancing gripping stability provided by the arrangement of ribs 320, 324 on the housing 310 of the valve assembly 350.

Delineation of the gripping areas 322 on the housing 310 of the valve assembly 350, and the sizing and/or positioning of the gripping areas 322 defined by the ribs 320, 324 on the housing 310 of the valve assembly 350, may guide finger and/or thumb placement for gripping the pump assembly 300, may facilitate location of the button component 312 on the valve assembly 350, and may provide stability as the button component 312 is manipulated by the user.

In some examples, a plurality of ribs 330 is defined on the outer surface of the pump bulb 308. Recesses 332 defining gripping areas may be formed between sets of ribs 320 on the pump bulb 308. For example, a first recess 332A defining a first gripping area may be formed between a first pair of first ribs 330A on a first portion of the pump bulb 308. A second recess 332B defining a second gripping area may be formed between a second set of first ribs 330B on a second portion of the pump bulb. A third recess 332B defining a third gripping area may be formed between a third pair of first ribs 330C on a third portion of the pump bulb 308. A fourth recess 332D defining a fourth gripping area may be formed between a fourth pair of first ribs 330D on a fourth portion of the pump bulb 308.

In some examples, the recesses 332 may be further defined by second ribs 334 positioned between adjacent recesses 332 and adjacent pairs of first ribs 330, so as to separate the adjacent recesses 332 and further delineate the gripping areas. The placement of the ribs 330, 334 and the recesses 332 defining the gripping areas in this manner may provide for stability in the griping of the pump bulb 308 during user manipulation of the pump bulb 308 (for example, squeezing and releasing of the pump bulb 308).

In the example shown in FIGS. 3A and 3B, the first ribs 330 on the pump bulb 308 have an arcuate, or curved shape, such that corresponding peripheral portions of the recesses 332 defining the gripping areas on the pump bulb 308 have a corresponding arcuate, or curved contour. The arcuate, or curved contour of the recesses 332 defining the gripping areas on the pump bulb 308 may result in gripping areas having a shape that accommodates finger and/or thumb placement, thus further enhancing gripping stability provided by the arrangement of ribs 330, 334 on the pump bulb 308.

Figure 4C:
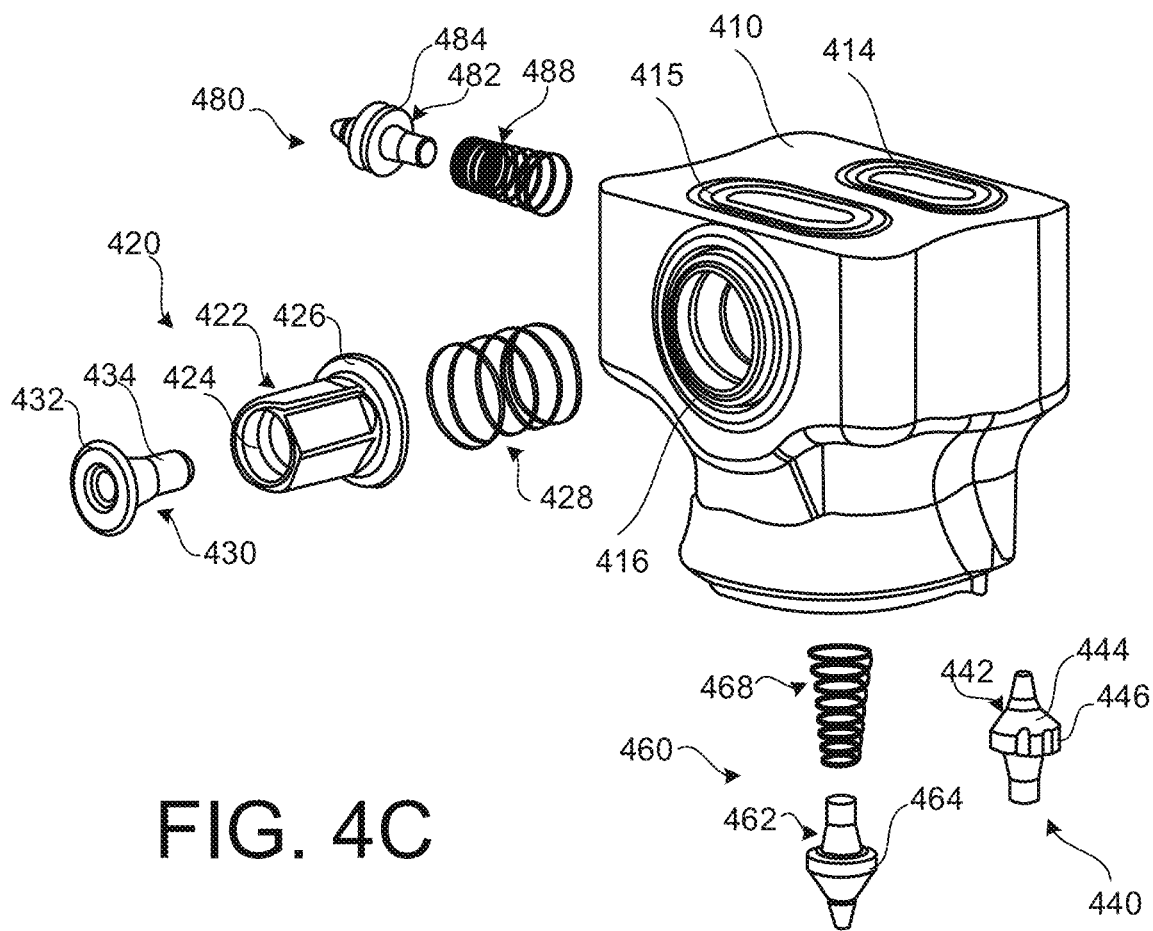

As shown in FIGS. 4A-4C, in some examples, a valve block 410 is received within the valve assembly housing 310. A plurality of valve components may be positioned in fluid passageways defined in the valve block 410. In some examples, the plurality of valve components includes a control valve 420, a refill valve 440, an inflation valve 460, and an anti-auto inflation valve 480. The relative positioning of the plurality of valve components within fluid passageways in the valve block 410/valve assembly housing 310 will be described below in more detail with respect to FIGS. 4C through 6B.

The control valve 420 may be movably received in a first passageway 620, or a control valve passageway 620 (see FIGS. 6A and 6B) formed in the valve block 410, at a position corresponding to the button component 312 of the housing 310 of the valve assembly 350. Elements of the control valve 420 may move within the first passageway 620 in response to an external force applied to the button component 312, such as, for example, a depression of the button component 312 by the user. In some examples, the control valve 420 includes a first movable member 422 and a second movable member 430. The first and second movable members 422, 430 may be movable relative to each other. In some examples, the first movable member 422 is a control valve body 422, and the second movable member 430 is a pin 430. A biasing member 428 biases the control valve body 422 to a closed position of the control valve 420. The control valve body 422 includes an opening defining a cavity 424 in the control valve body 422. The pin 430 is slidably received in the cavity 424. For example, the pin 430 may be slidably received into the cavity 424 through the opening in the first end portion of the control valve body 422. A flange 426 extends along an outer periphery of a second end portion of the control valve body 422. An end of the biasing member 428 may be positioned against the flange 426 in an assembled state of the control valve 420. In some examples, the pin 430 includes a base portion 432, or head portion 432 and a protruded portion 434, or a shaft portion 434. In some examples, the pin 430 is coupled to the button component 312. In some examples, the pin 430 is formed as a single unit with the button component 312.

The refill valve 440 may be received in a second passageway 640, or a refill valve passageway 640, formed in the valve block 410. The refill valve 440 includes a refill valve body 442. In some examples, the refill valve body 442 may be shaped or contoured so as to guide fluid flow through the second passageway 640, to stabilize fluid flow through the second passageway 640, and to reduce or substantially eliminate jitter of the refill valve body 442 as fluid flows through the second passageway 640. For example, a protrusion 444 may extend along an outer periphery of an intermediate portion of the refill valve body 442. In some examples, the protrusion 444 includes a first surface that extends at an incline from an inclined tip portion of the refill valve body 442. In some examples, one or more grooves 446 are formed on a second surface of the protrusion 444, extending in a flow direction of fluid through the second passageway 640. In some examples, the grooves 446 are positioned intermittently along substantially the entire outer periphery of the second surface of the protrusion 444. In some examples, the grooves 446 are formed in only a portion of the outer periphery of the second surface of the protrusion 444. In some examples, the second passageway 640 is shaped or contoured to correspond to a shape or contour of the refill valve 440. In some examples, the second passageway 640 includes fluting 646 that helps to guide the flow of fluid through the second passageway 640 and past the refill valve 440. In some examples, the fluting 646 is defined by protrusions and/or recesses in the contour of the second passageway 640. In some examples, the fluting 646 extends in a direction of fluid flow through the second passageway 640. In some situations, the external shape of the refill valve body 442, including the grooves 446 of the refill valve body 442 and/or the fluting 646 of the second passageway 640, may provide for uniform flow, may guide the flow of fluid through the second passageway 640, and may reduce flow instability through the second passageway 640.

The inflation valve 460 may be received in a third passageway 660, or an inflation valve passageway 660, formed in the valve block 410. In some examples, the inflation valve 460 includes an inflation valve body 462 and an inflation valve biasing member 468. The biasing member 468 biases the inflation valve body 462 to a closed position of the inflation valve 460. A protrusion 464 may extend along an outer periphery of an intermediate portion of the inflation valve body 462. An end of the biasing member 468 may be positioned against the protrusion 464 in an assembled state of the inflation valve 460. In some examples, the inflation valve body 462 may be shaped or contoured so as to guide fluid flow through the third passageway 660, to stabilize fluid flow through the third passageway 660, and to reduce or substantially eliminate jitter of the inflation valve body 462 as fluid flows through the third passageway 660. For example, the protrusion 464 may include a first surface that extends at an incline from an inclined tip portion of the inflation valve body 462. In some examples, one or more grooves 466 are formed on a second surface of the protrusion 464, extending in a flow direction of fluid through the third passageway 660. In some examples, the third passageway 660 includes fluting 666 that helps to guide the flow of fluid through the third passageway 660 and past the inflation valve 460. In some examples, the fluting 666 is defined by protrusions and/or recesses in the contour of the third passageway 660. In some examples, the fluting 666 extends in a direction of fluid flow through the third passageway 660. In some situations, the external shape of the inflation valve body 462, together with the fluting 666 may provide for uniform flow, may guide the flow of fluid through the third passageway 660, may reduce flow instability through the third passageway 660, and may reduce jitter of the valve body 422 as fluid flows through the third passageway 660.

The anti-auto inflation valve 480 may be received in a fourth passageway 680, or an anti-auto inflation valve passageway 680, formed in the valve block 410. In some examples, the anti-auto inflation valve 480 includes an anti-auto inflation valve body 482 and an anti-auto inflation valve biasing member 488. The biasing member 488 biases the valve body 482 to a closed position of the anti-auto inflation valve 480. A protrusion 484 may extend along an outer periphery of an intermediate portion of the valve body 482. An end of the biasing member 488 may be positioned against the protrusion 484 in an assembled state of the anti-auto inflation valve 480. In some examples, the valve body 482 may be shaped or contoured so as to guide fluid flow through the fourth passageway 680, to stabilize fluid flow through the fourth passageway 680, and to reduce or substantially eliminate jitter of the valve body 482 as fluid flows through the fourth passageway 680. For example, the protrusion 484 may include a first surface that extends at an incline from an inclined tip portion of the valve body 482. In some examples, one or more grooves 486 may be formed on a second surface of the protrusion 484, extending in a flow direction of fluid through the fourth passageway 680. In some examples, the fourth passageway 680 includes fluting 686 that helps to guide the flow of fluid through the fourth passageway 680 and past the anti-auto inflation valve 480. In some examples, the fluting 686 is defined by protrusions and/or recesses in the contour of the fourth passageway 680. In some examples, the fluting 686 extends in a direction of fluid flow through the fourth passageway 680. In some situations, the external shape of the valve body 482, together with the fluting 686, may provide for uniform flow, may guide the flow of fluid through the fourth passageway 680, and may reduce flow instability through the fourth passageway 680.

Figure 7A:
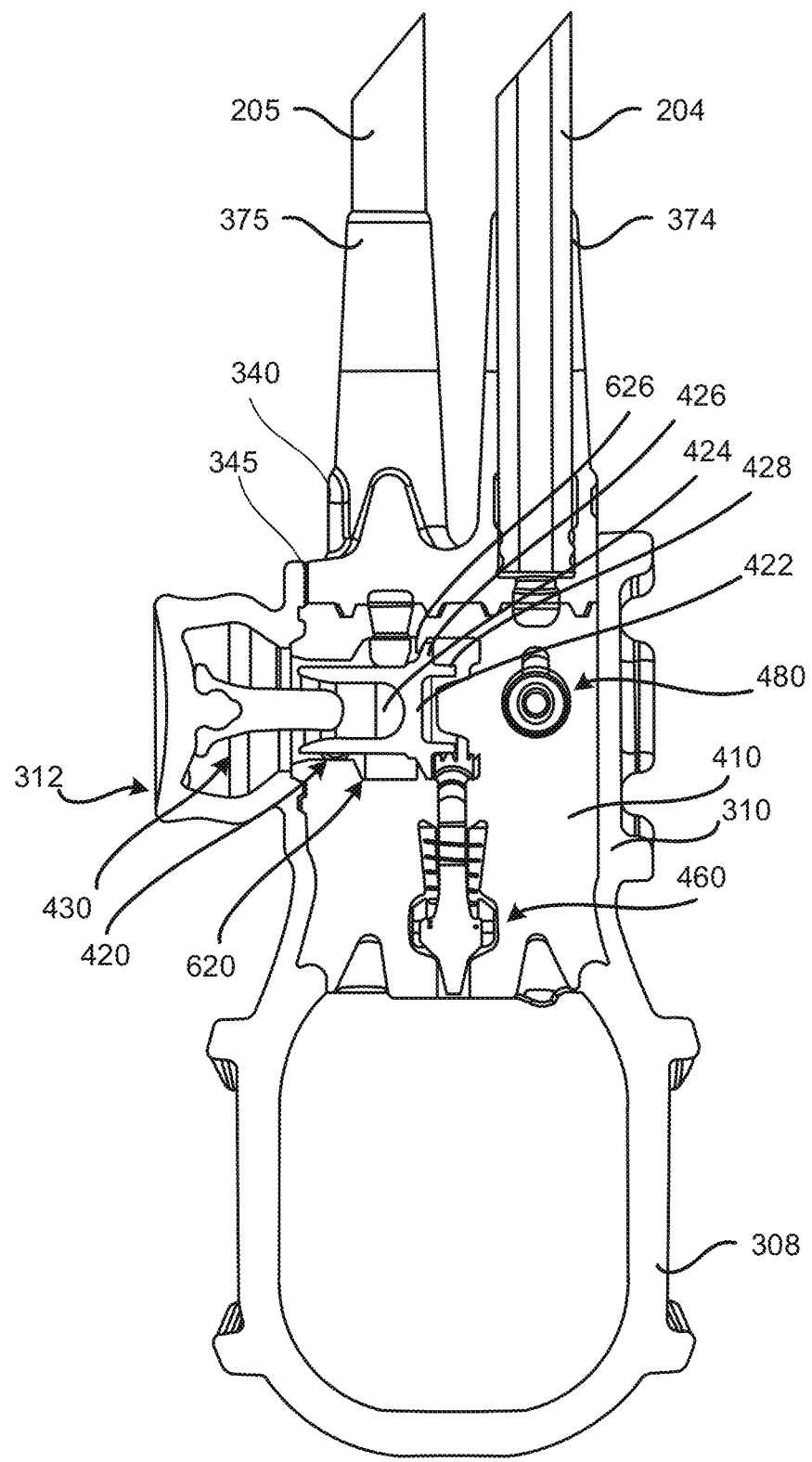
FIG. 7A is a cross-sectional view of the example pump assembly shown in FIGS. 3A and 3B, taken along line A-A of FIG. 3A, illustrating the positioning of valve components of the example pump assembly in an idle state.
Figure 7B:
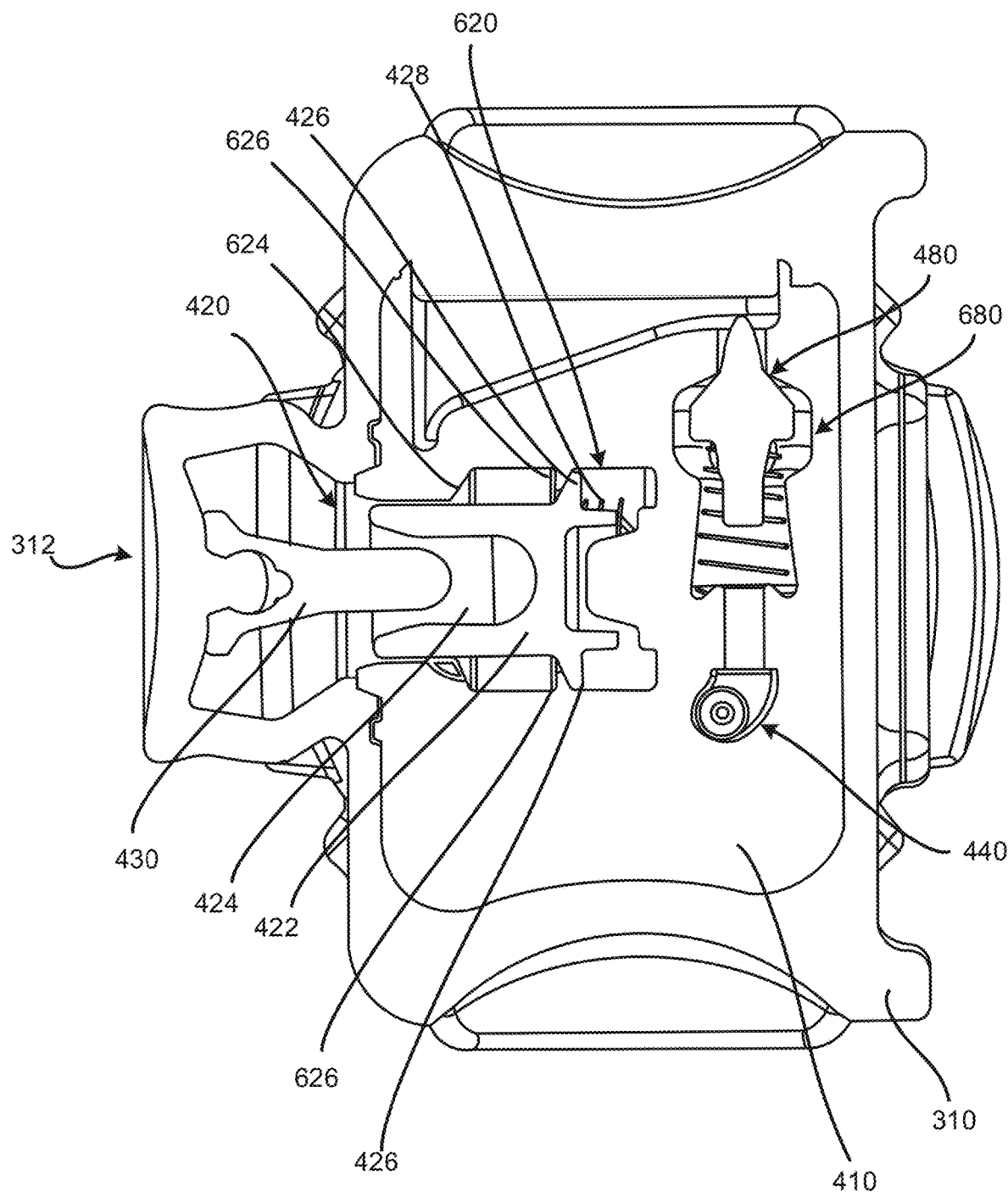
FIG. 7B is a cross-sectional view of the example pump assembly shown in FIGS. 3A and 3B, taken along line B-B of FIG. 3A, illustrating the positioning of valve components of the example pump assembly in an idle state.

FIG. 7A is a cross-sectional view taken along line A-A of FIG. 3A. FIG. 7B is a cross-sectional view taken along line B-B of FIG. 3A. In an idle state, or an at rest state, in which the user has not actuated the pump assembly 300 to cause inflation of the cylinders 290, the components within the valve block 410 are positioned as shown in FIGS. 7A and 7B. That is, in the idle state, the control valve body 422 is positioned in the first passageway 620 so as to control, for example, restrict or block the flow of fluid from the reservoir 202 to the cylinders 290. In the idle state, the inflation valve 460 is positioned in the third passageway 660 so as to control, for example, restrict or block the flow of fluid from the pump bulb 308 to the cylinders 290.

In the idle state, or the at rest state, shown in FIGS. 7A and 7B, the flange 426 of the control valve body 422 is positioned against a positioning lip 626, or a holding lip 626, or a first lip 626 defined on a wall surface of the first passageway 620. The positioning of the flange 426 of the control valve body 422 against the first lip 626 of the first fluid passageway 620 maintains an idle fluid state. In the idle fluid state, fluid may be retained, for example, in the reservoir 202, and does not flow through the first fluid passageway 620 and into a fifth passageway 650 (see FIGS. 6A and 6B) leading to the second port 415 and the cylinders 290. Similarly, in the idle fluid state, fluid does not flow from the first passageway 620, through the second passageway 640 and into the pump bulb 308.

Figure 8A:
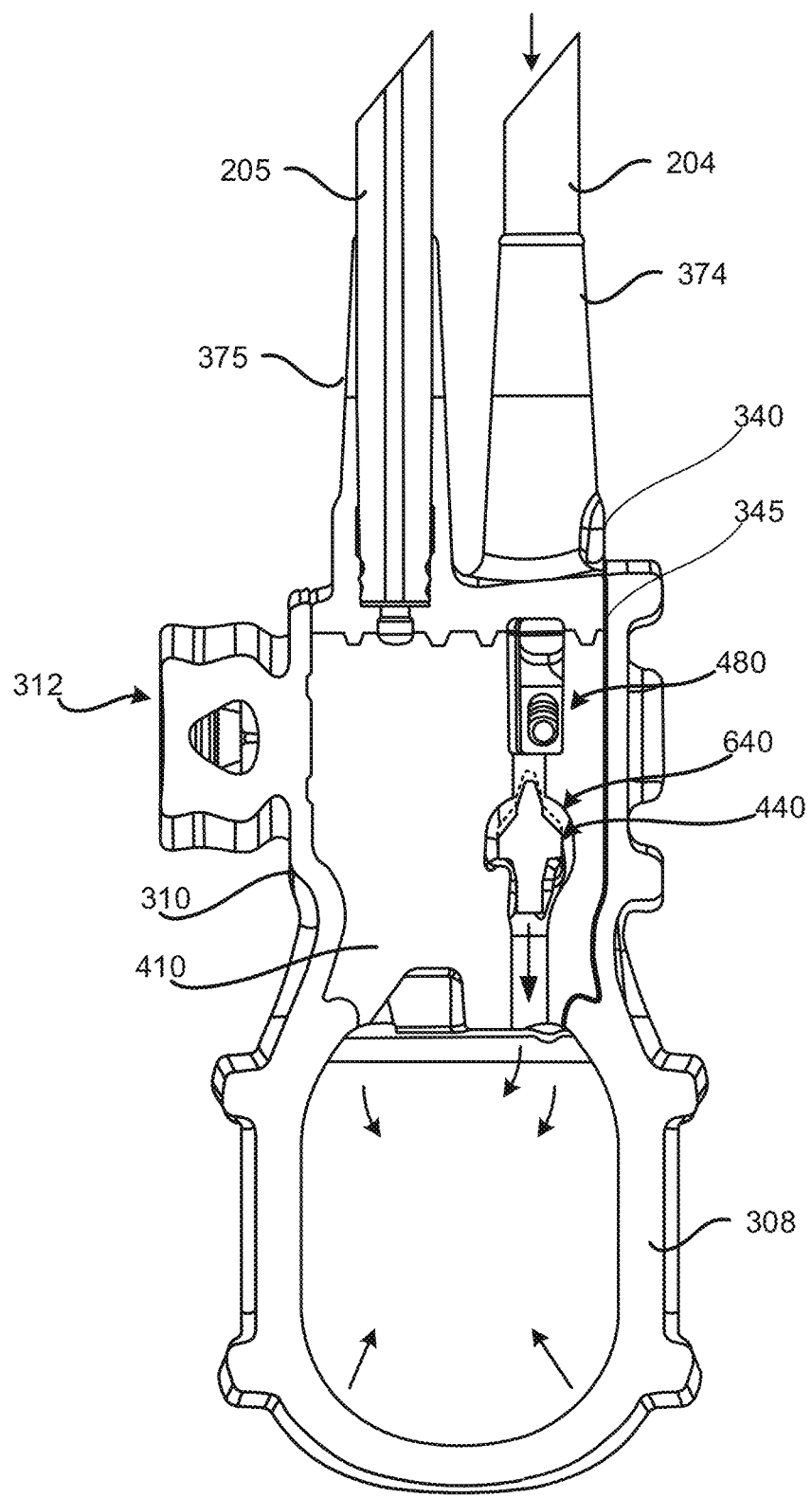
FIG. 8A is a cross-sectional view of the example pump assembly shown in FIGS. 3A and 3B, taken along line C-C of FIG. 3A, illustrating the positioning of valve components of the example pump assembly in an inflation mode of operation.
Figure 8B:
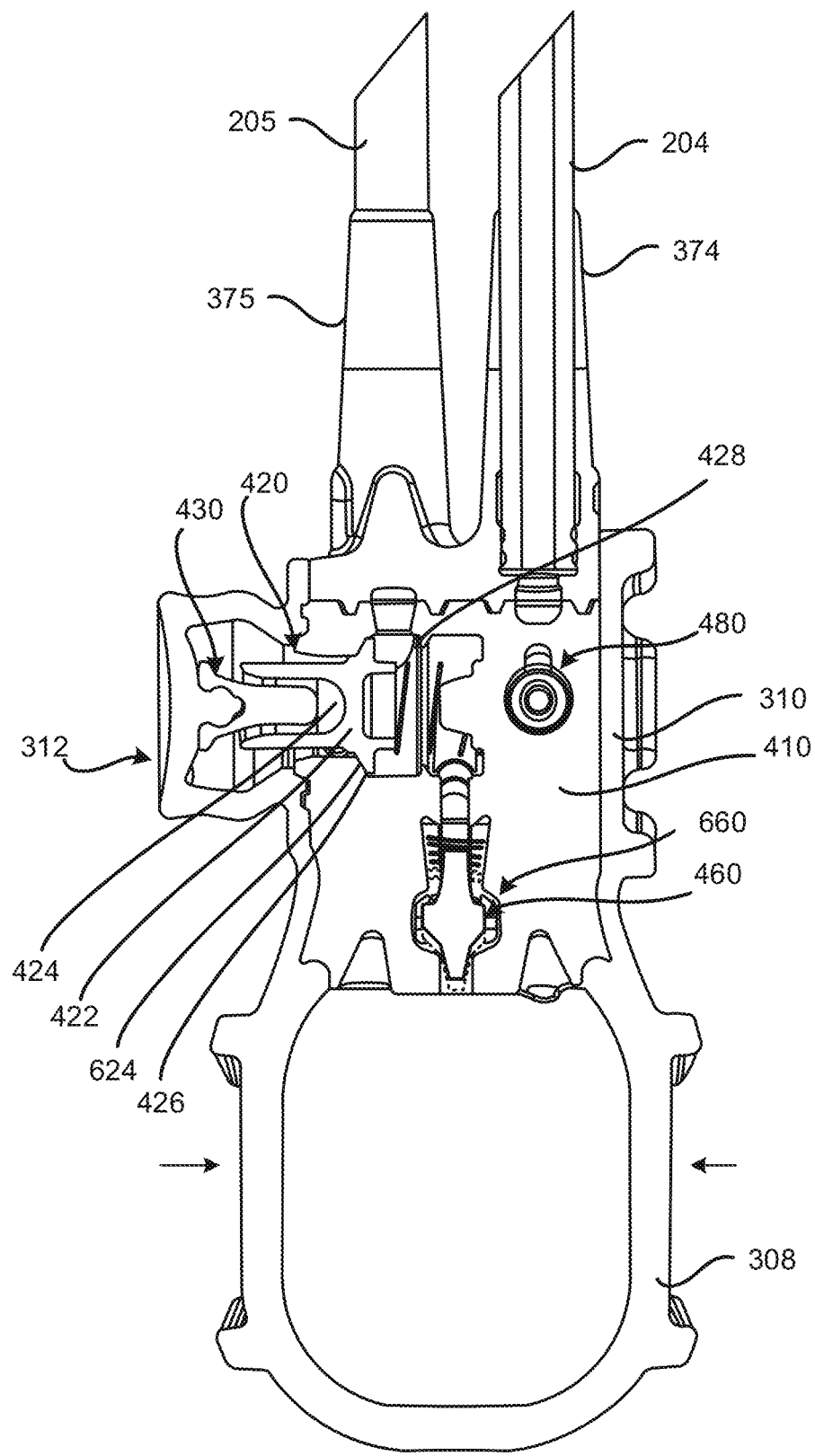
FIG. 8B is a cross-sectional view of the example pump assembly shown in FIGS. 3A and 3B, taken along line B-B of FIG. 3A, illustrating the positioning of valve components of the example pump assembly in an inflation mode of operation.

FIGS. 8A and 8B are cross-sectional views illustrating the inflation mode of the pump assembly 300. FIG. 8A is a cross-sectional view taken along line C-C of FIG. 3A, illustrating a position of the refill valve 440 in the second passageway 640 for the transfer of fluid from the reservoir 202 to the pump bulb 308. FIG. 8B is a cross-sectional view taken along line A-A of FIG. 3A, illustrating position of the control valve 420 in the first passageway 620 and the inflation valve 460 in the third passageway 660 for the transfer of fluid from the pump bulb 308 to the cylinders 290.

In some examples, in the inflation mode, fluid is accumulated in the pump bulb 308, and the accumulated fluid is expelled from the pump bulb 308 and transferred to the cylinders 290 to inflate the cylinders 290. To inflate the cylinders 290 (from the at rest state) the user may manipulate, for example, squeeze and release, the pump bulb 308. In an empty state of the pump bulb 308, the pressure differential between the reservoir 202 and the pump bulb 308 (generated in response to the manipulation of the pump bulb 308) may cause the refill valve 440 to move from a first position (shown in dotted lines in FIG. 8A) in which the spring 448 biases the refill valve body 442 to seal the second passageway 640, to a second position (shown in solid lines in FIG. 8A) in which the second passageway 640 is open, allowing fluid to flow into the pump bulb 308. In some examples, the refill valve 440 is a one-way valve, so that fluid can flow from the reservoir 202 to the pump bulb 308 in the manner described above, but due to the configuration of the refill valve 440, fluid does not flow from the pump bulb 308 back to the reservoir 202.

With fluid filled in the pump bulb 308, the user may further manipulate, for example, squeeze and release, the pump bulb 308 to transfer fluid from the pump bulb 308 to the cylinders 290, as shown in FIG. 8B. That is, further manipulation of the pump bulb 308 forces fluid into the third passageway 660. The pressure of the fluid causes the inflation valve 460 to move from a first position (shown in dotted lines in FIG. 8B) in which the spring 468 biases the inflation valve body 462 to seal the third fluid passageway 660, to a second position (shown in solid lines in FIG. 8B) in the third passageway 660 is open. In some examples, the flange 426 of the control valve 420 abuts a sealing surface 624, or a sealing lip 624, or a second lip 624 in the wall of the first fluid passageway 620 in the inflation mode. The flow of fluid through the third fluid passageway 660 and into the first fluid passageway 620 forces disengagement of the flange 426 of the control valve 420 from the first lip 626 in the first fluid passageway 620, moving the control valve body 422 (to the left in the orientation shown in FIG. 8B). This movement of the control valve body 422 allows fluid to flow through the first passageway 620 and the fifth fluid passageway 650 for through the second port 415 for inflation of the cylinders 290.

To initiate the deflation mode of operation of the pump assembly 300, the user may manipulate, for example, depress the button component 312. In some examples, the manipulation to initiate the deflation mode includes a single depression and release of the button component 312. In some examples, the manipulation to initiate the deflation mode includes a sustained single depression. In some examples, the manipulation to initiate the deflation mode includes repeated depression and release of the button component 312 until the deflation process is complete.

FIGS. 9A and 9B are cross-sectional views illustrating movement of the control valve 420 in response to this type of manipulation of the button component 312. From the position of the control valve 420 in the inflation mode shown in FIG. 9A, the user may apply a force F to the button component 312, causing a corresponding movement of the control valve 420, from the position shown in FIG. 9A, to the position shown in FIG. 9B. In the position shown in FIG.

9B, the flange 426 of the control valve body 422 is once again engaged with the lip 626 formed in the first fluid passageway 620.

Figure 10A:
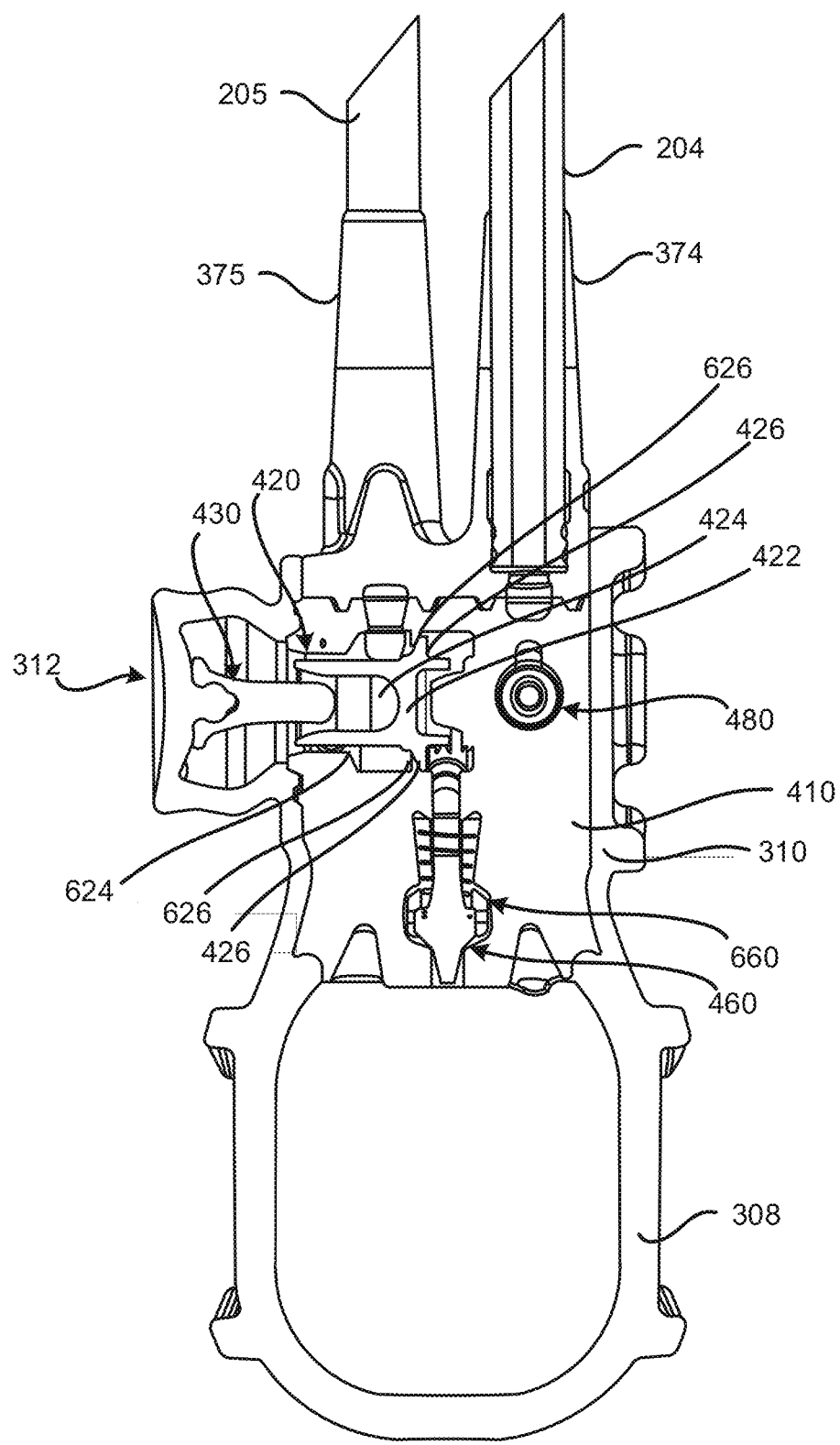
FIG. 10A is a cross-sectional view taken along line A-A of FIG. 3A.
Figure 10B:
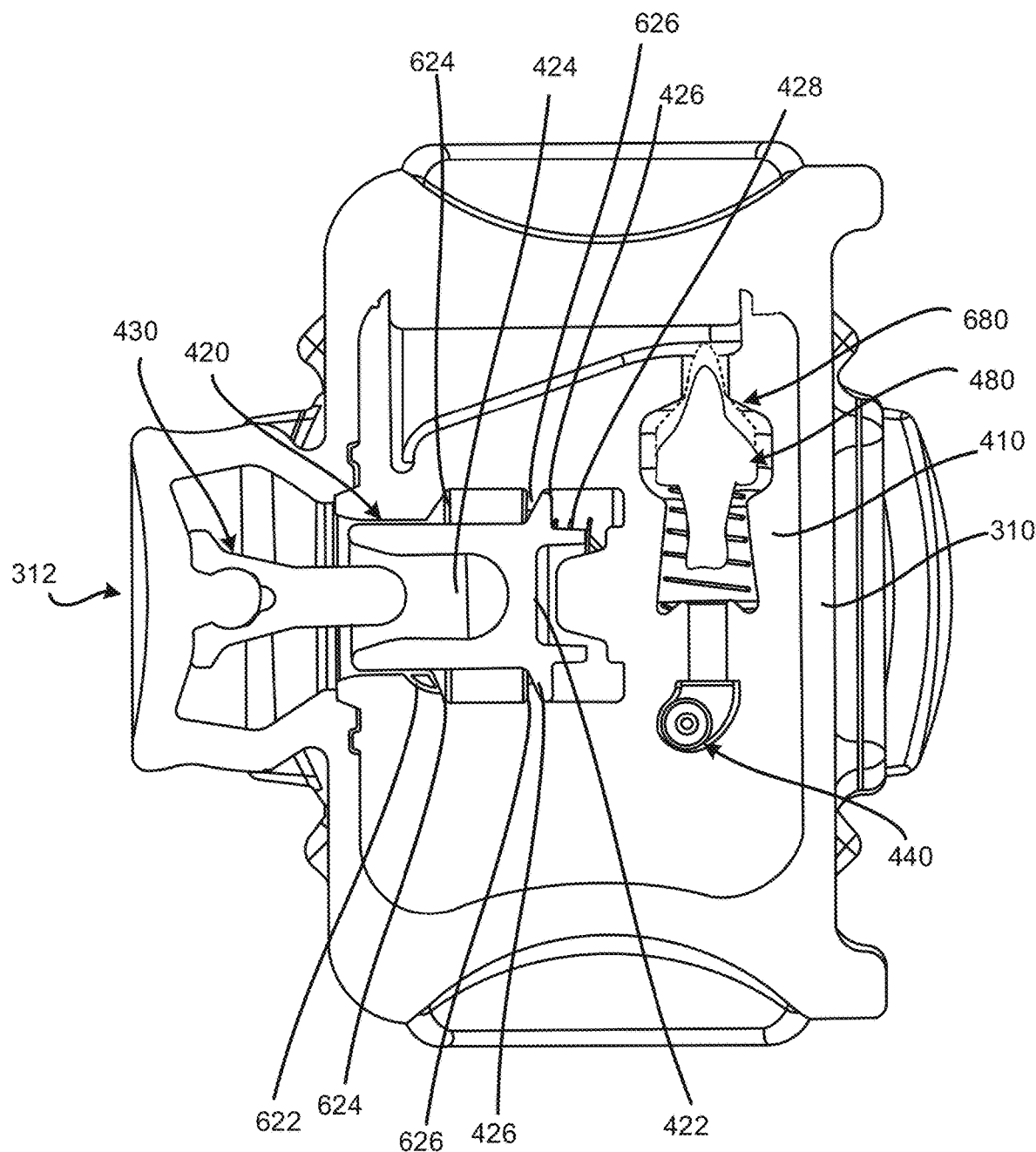
FIG. 10B is a cross-sectional view taken along line B-B of FIG. 3A, illustrating the positioning of valve components of the example pump assembly in a deflation mode of operation.

FIG. 10A is a cross-sectional view taken along line A-A of FIG. 3A, and FIG. 10B is a cross-sectional view taken along line B-B of FIG. 3A, illustrating the positioning of the valve components of the valve assembly 350 in the deflation mode of the pump assembly 300. In the deflation mode, the flange 426 of the control valve body 422 is once again engaged with the first lip 626 formed in the first fluid passageway 620, and the spring 468 biases the inflation valve body 462 to restrict fluid flow between the pump bulb 308 and the third passageway 660, thus restricting between the valve block 410 and the pump bulb 380. In the deflation mode, fluid is forced back to the reservoir 202. The force of the fluid causes the anti-auto inflation valve 480 to move from a position in which the spring 488 biases the valve body 482 of the anti-auto inflation valve 480 to a closed position (shown in dotted lines in FIG. 10B), to an open position (shown in solid lines) that allows fluid to flow through a sixth fluid passageway 670 for discharge through the first port 414 to the reservoir 202.

Figure 11:
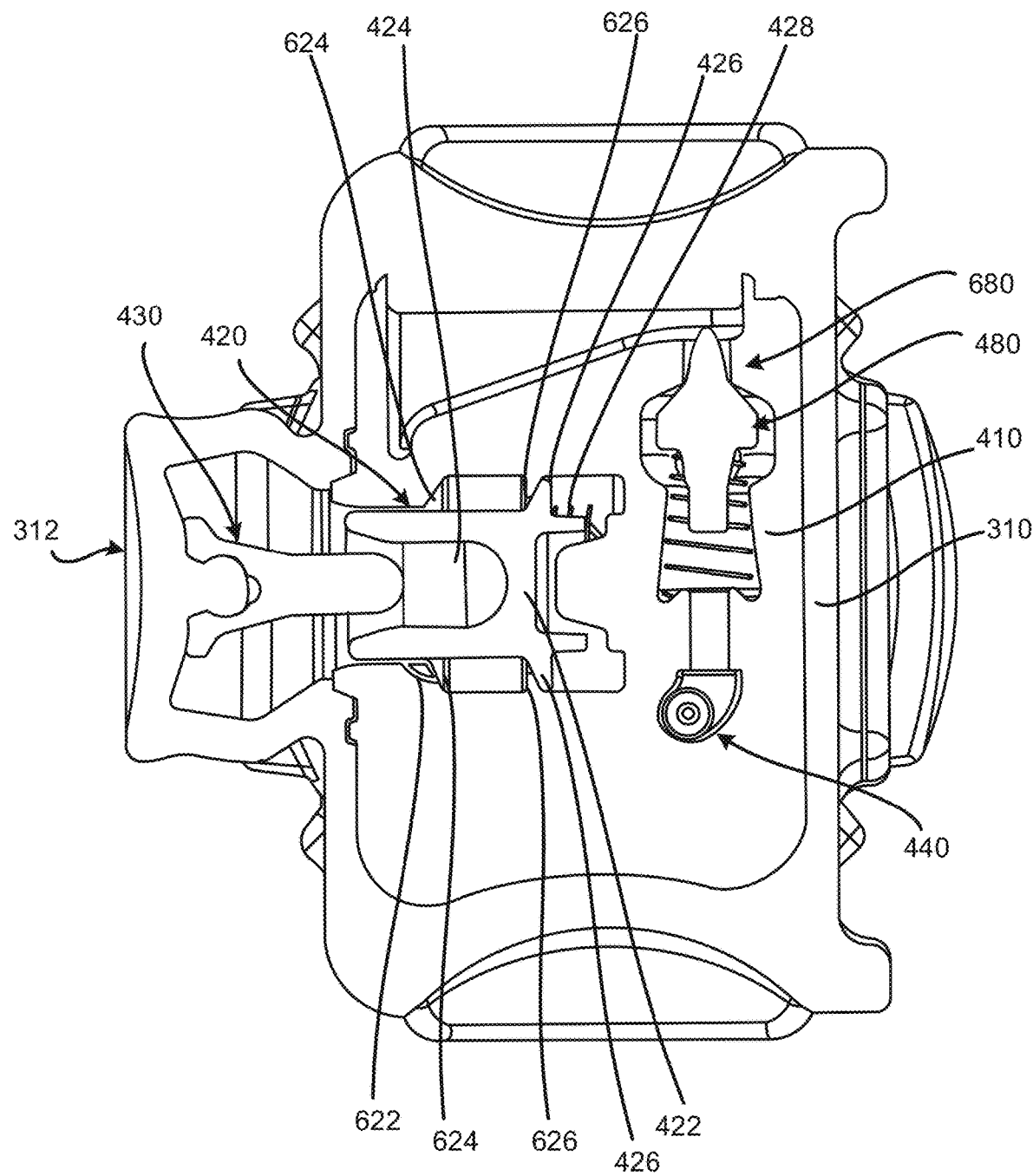
FIG. 11 is a cross-sectional view taken along line B-B of FIG. 3A, illustrating operation of an example anti-auto inflation valve of the example pump assembly.

In some examples, components of the pump assembly 300 are positioned so as to prevent inflation of the inflatable cylinders 290 without deliberate user actuation of the pump assembly 300. In an anti-auto inflation mode of operation, fluid, for example, the majority of the fluid, may be held in the reservoir 202 and the first conduit connector 204, and flow of fluid through the pump assembly 300 to the cylinders 290 is restricted based on the relative positioning of the valve components of the valve assembly 350. For example, as shown in FIG. 11, the position of the control valve 420 and the anti-auto inflation valve 480 restricts fluid held in the reservoir 202 from flowing through the valve block 410 to the cylinders 290. In this mode, the control valve 420 is positioned in the first passageway 620 with the biasing member 488 biasing the valve body 482 of the anti-auto inflation valve 480 to a position, to retain fluid in the reservoir 202, so that the cylinders 290 cannot be unintentionally inflated. In this arrangement, the anti-auto inflation valve 480 is only in an open position when the cylinders 290 are inflated, or under pressure. This provides for an open flow of fluid between the cylinders 290 and the reservoir 202, bypassing the pump bulb 308. In some examples, the anti-auto inflation valve 480 is a one-way valve, such that the anti-auto inflation valve 480 prevents fluid from flowing from the reservoir 202 to the cylinders 290 when the pump assembly 300 is in the deflation mode.

Figure 12:
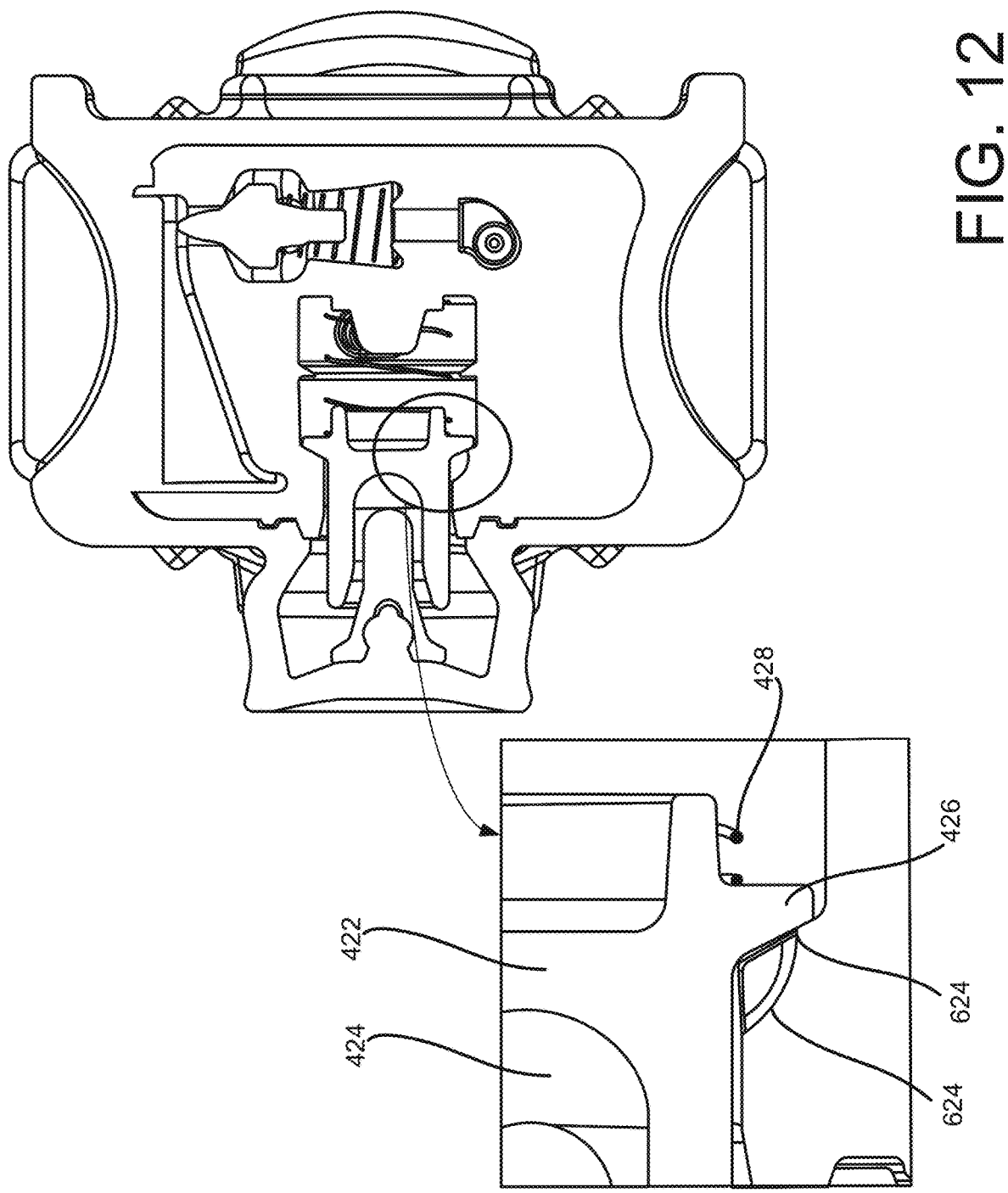
FIG. 12 illustrates an example pressure relief channel of the example pump assembly.

As shown in FIG. 12, in some examples, the first passageway 620 in which the control valve 420 is received includes a pressure relief channel 622. The pressure relief channel 622 may be formed in the wall of the first passageway 610, adjacent to the second lip 624 that engages the flange 426 of the control valve 420 in the inflation position (see FIG. 8B). In some examples, the pressure relief channel 622 is defined as an annular recess formed in the wall of the first passageway 620. In some examples, the pressure relief channel 622 is defined by one channel formed in the wall of the first passageway 620. In some examples, the pressure relief channel 622 includes multiple channels formed in the wall of the first passageway 620. In some situations, an excess of fluid pressure in the first passageway 620 may accumulate in the first passageway 620, for example, a fluid pressure that is greater than a threshold pressure which will cause disengagement of the flange 426 of the control valve body 422 and the lip 624 formed in the passageway 620. The excess of fluid pressure may be due to, for example, continued manipulation of the pump bulb 308, producing fluid pressure buildup beyond what can be processed by the control valve 420 and/or beyond what is necessary to inflate the cylinders 290. This fluid pressure greater than the threshold may force disengagement of the flange 426 of the control valve body 422 and the lip 624 formed in the passageway 620. Disengagement of the flange 426 and the lip 624 and continued fluid pressure could result in misalignment of the valve body 422 in the first passageway 620. Misalignment may cause the valve body 422 to remain stuck in the misaligned position thus limiting the ability to move the control valve 420 to the deflation position. The pressure relief channel 622 may be shaped and positioned so as to urge the valve body 422 back to the position shown in FIG. 8B.

Figure 13:
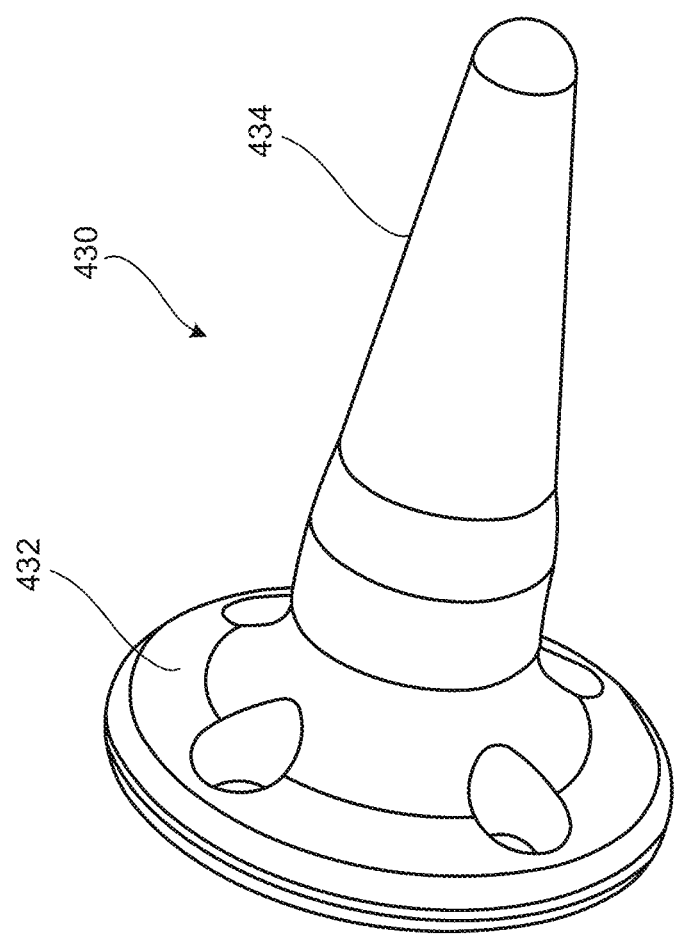
FIG. 13 is a perspective view of an example movable member of an example control valve of the example pump assembly, according to an aspect.

In some examples, the pin 430 is coupled to a portion of the housing 310 of the valve assembly 350 corresponding to the button component 312. For example, the pin 430 may be coupled to an interior portion of the housing 310, or co-formed with the corresponding portion of the housing 310, or formed as a single unit with the corresponding portion of the housing 310. In some examples, the material of the housing 310, particularly in the area of the button component 312, is a deformable material so as to support the depression of the button component 312 and the corresponding movement of the pin 430 into the cavity 424 of the valve body 422. FIG. 13 is a perspective view of the pin 430 described above, which may be movably, for example, slidably engaged with the valve body 422 of the control valve 420 to position the control valve 420 for operation of the pump assembly 300 in the inflation mode or the deflation mode. The pin 430 shown in FIG. 13 includes the base portion 432, or head portion 432 and the protruded portion 434, or shaft portion 434, as noted above. In some examples the shaft portion 434 of the pin 430 has a tapered contour defined by an inclined outer surface, such that a diameter of the shaft portion 434 gradually decreases with increasing distance from the head portion 432. For example, a diameter of the shaft portion 434 at a proximal end portion of the pin 430 is greater than a diameter of the shaft portion at a distal end portion of the pin 430. The tapered contour of the shaft portion 434 of the pin 430 may facilitate the alignment of the shaft portion 434 of the pin 430 into the cavity 424 defined in the valve body 422 of the control valve 420. In some examples, the shaft portion 434 of the pin 430 is elongated, such that at least a portion of the length of the shaft portion 434 remains received in the cavity 424 of the valve body 422, regardless of a position of the pin 430 relative to the valve body 422. That is, a length of the shaft portion 434 of the pin 430 may be long enough so that at least a portion of the shaft portion 434 remains engaged in the cavity 424, so as to maintain connection between the button component 312 and the control valve 420. For example, a length of the shaft portion 434 may be greater than a depth of the cavity 424. This may maintain alignment between the pin 430 and the valve body 422, and may facilitate the reliable switching between the inflation and deflation modes in response to depression of the button component 312 as described above.

FIGS. 14A and 14B are cross-sectional views of an example coupling of the pin 430 to the corresponding portion of the housing 310 of the valve assembly 350. In the example shown in FIGS. 14A and 14B, a button face 318 of the housing 310 includes an opening 316 to accommodate insertion of the pin 430. A size, for example, a diameter of the opening 316 may be large enough to accommodate insertion therethrough of the shaft portion 434 of the pin 430. A size, for example, a diameter of the opening be less than a diameter of the head portion 432, so that the head portion 432 may be engaged with the outer surface of the button face 318 of the housing 310. In some examples, an adhesive may be applied to mating surfaces of the head portion 432 of the pin 430 and the button face 318 prior to insertion of the pin 430 through the opening 316. This may improve the retention of the position of the pin 430 relative to the housing 310, which may in turn provide for consistency in the positioning of the shaft portion 434 relative to the cavity 424 of the valve body 422, thus enhancing reliability in operation. Further, as noted above, the elongation of the shaft portion 434 of the pin 430 may maintain alignment and engagement of the pin 430 and control valve 420, both in the released state of the button component 312 shown in FIG. 14A, and in the depressed state of the button component 312 shown in FIG. 14B.

Figure 15A:
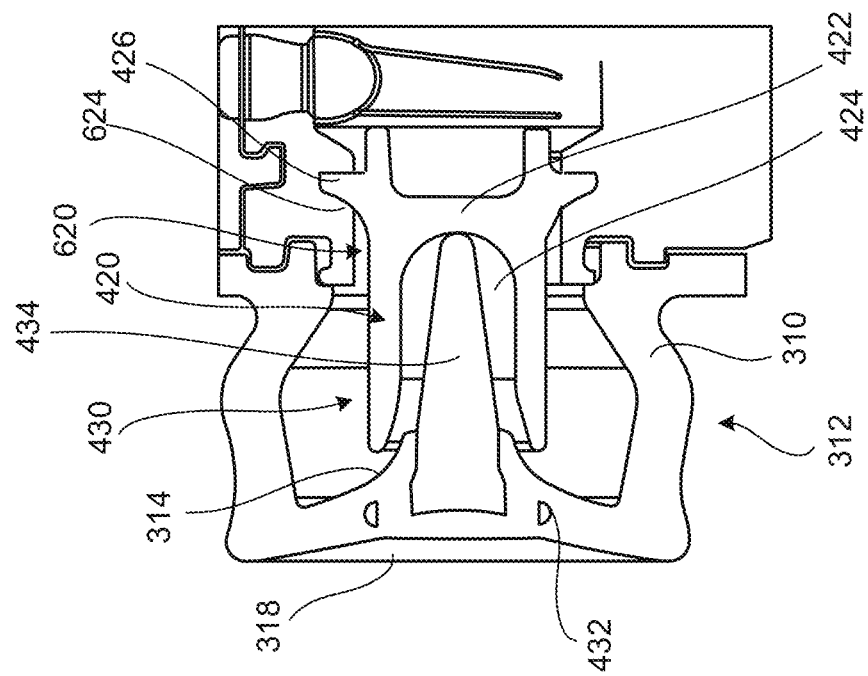
FIGS. 15A and 15B are cross-sectional views of example first and second movable members of an example control valve of the example pump assembly, according to an aspect.
Figure 15B:
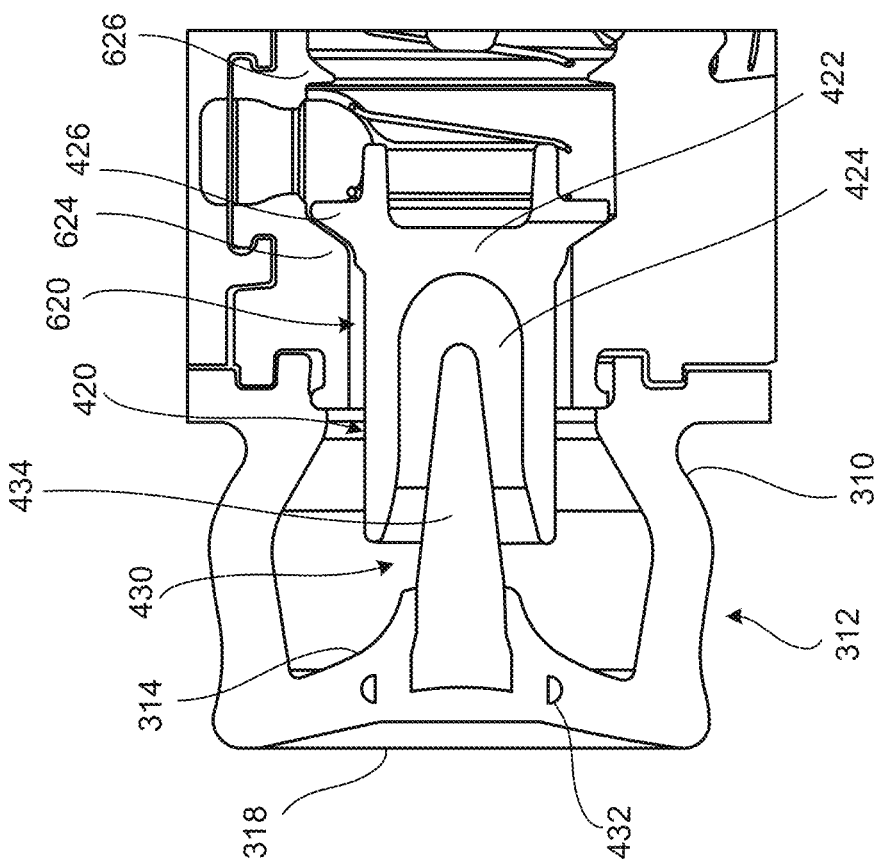

FIGS. 15A and 15B are cross-sectional views of another example coupling of the pin 430 to the corresponding portion of the housing 310 of the valve assembly 350. In the example shown in FIGS. 15A and 15B, the head portion 432 of the pin 430 is over-molded with the material of the housing 310 of the valve assembly 350 as the housing 310 is fabricated. In this example, an over-molded portion 314 retains the head portion 432 of the pin 430 with respect to the housing 310. In this example, the shaft portion 434 may be coupled to the head portion 432 of the pin 430 after the over-molding is complete and the over-molded portion 314 fixes a position of the head portion 432 of the pin 430. This arrangement may improve the retention of the position of the pin 430 relative to the housing 310, which may in turn provide for consistency in the positioning of the shaft portion 424 relative to the cavity 424 of the valve body 422, thus enhancing reliability in operation. Further, as noted above, the elongation of the shaft portion 434 of the pin 430 may maintain alignment and engagement of the pin 430 and control valve 420, both in the released state of the button component 312 shown in FIG. 15A, and in the depressed state of the button component 312 shown in FIG. 15B.

Figure 16:
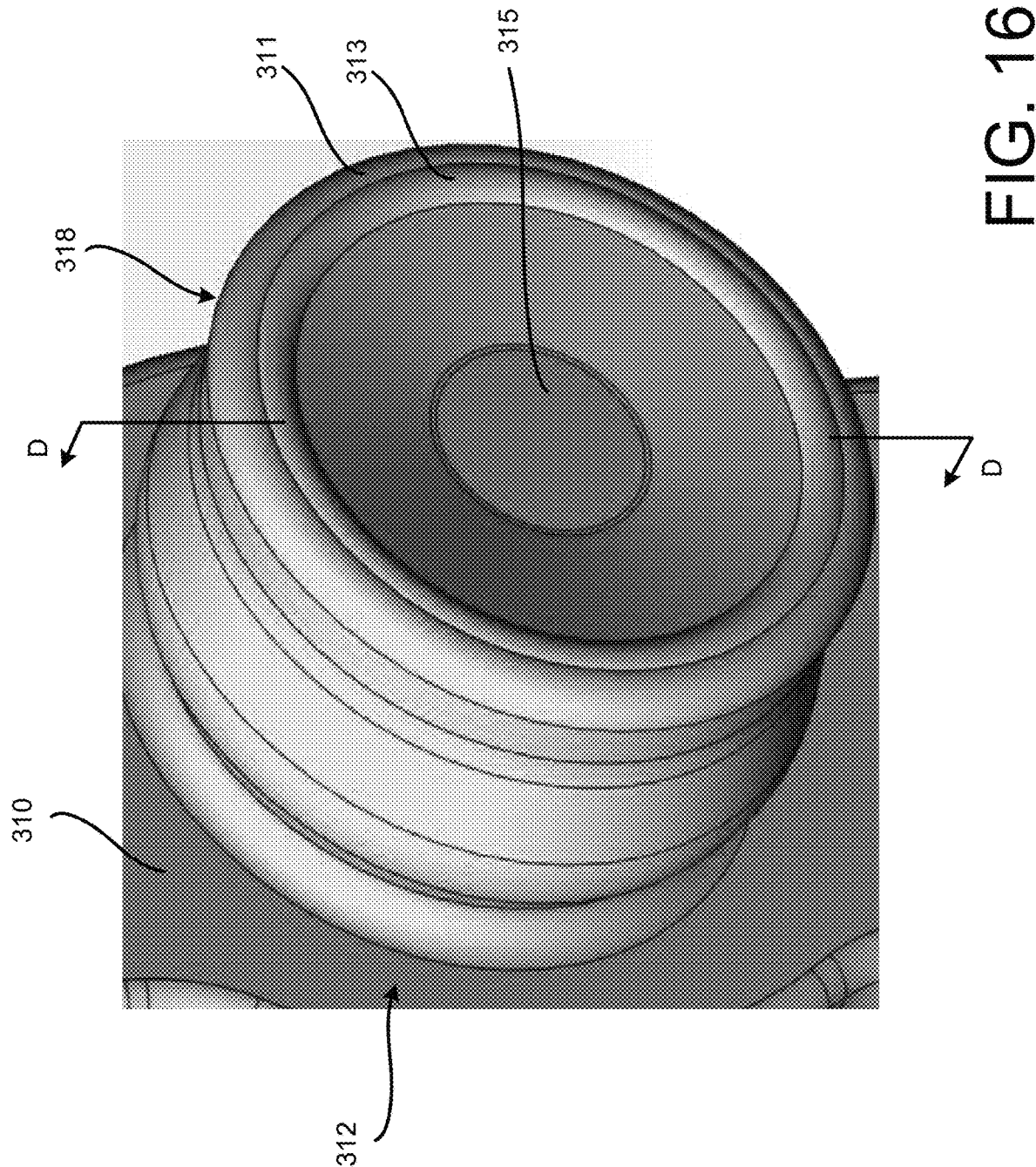
FIG. 16 is a perspective view of a button component of the example pump assembly, according to an aspect.
Figure 17:
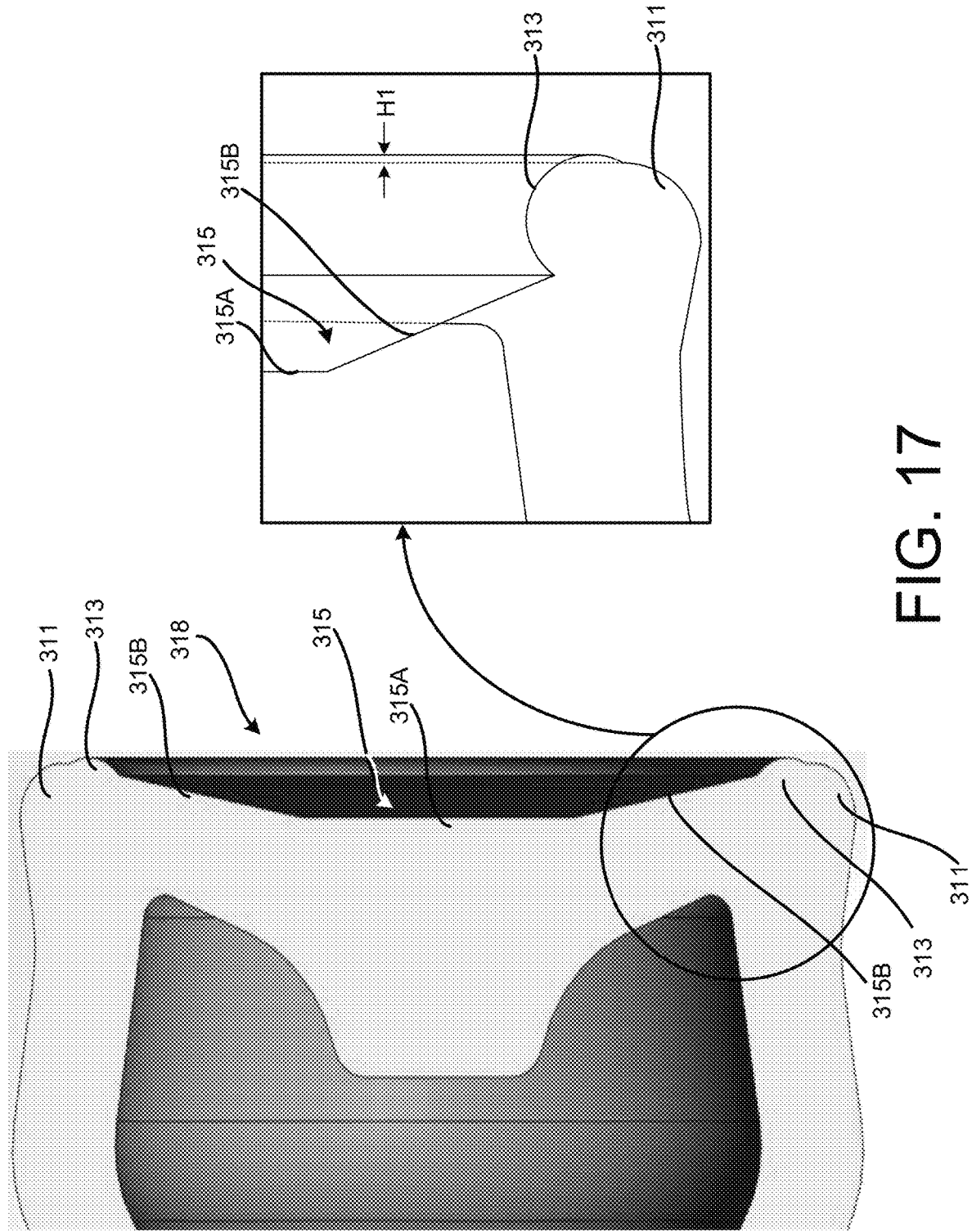
FIG. 17 is a cross-sectional view taken along line D-D of FIG. 16.
Figure 18:
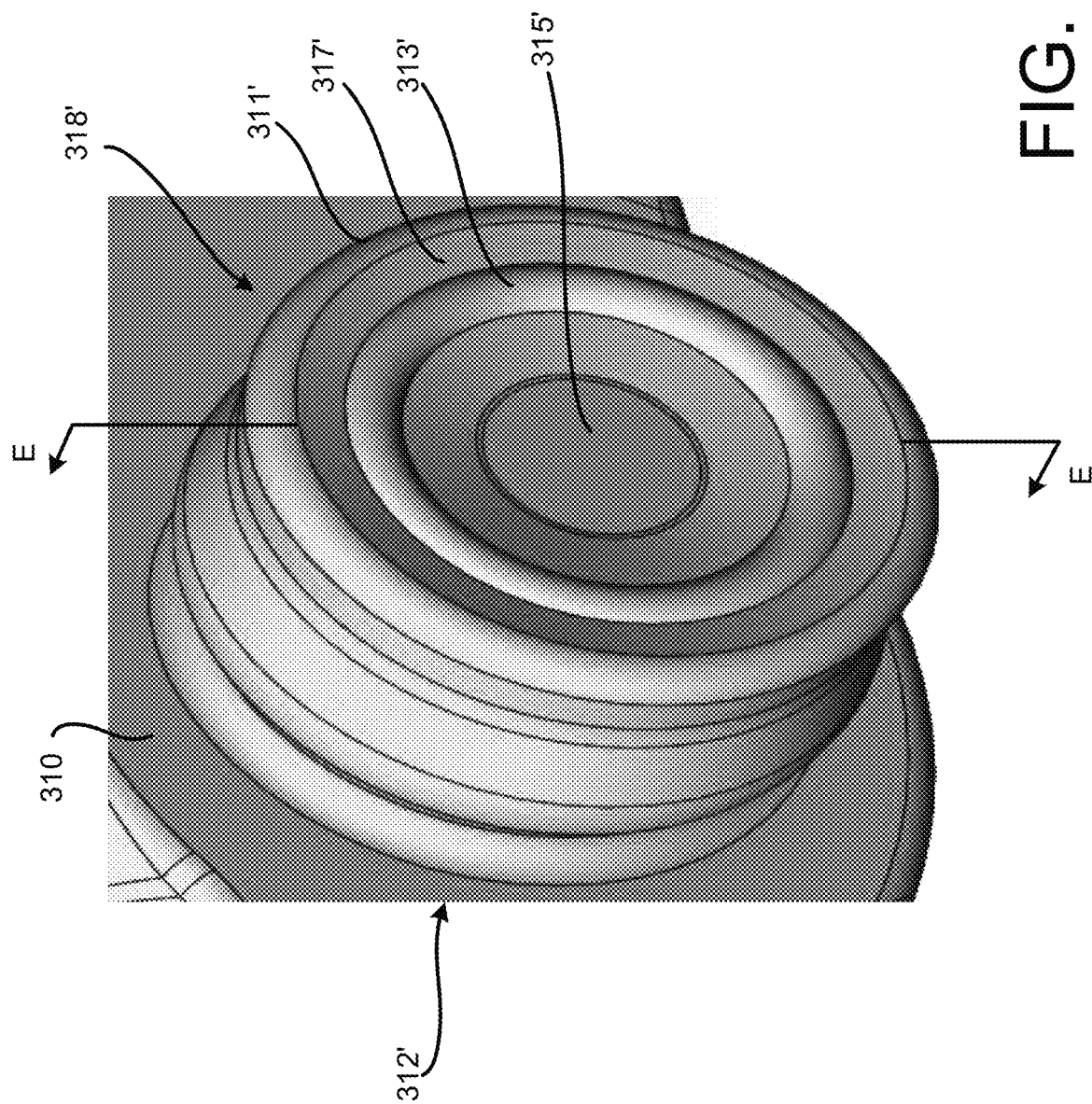
FIG. 18 is a perspective view of a button component of the example pump assembly, according to an aspect.
Figure 19:
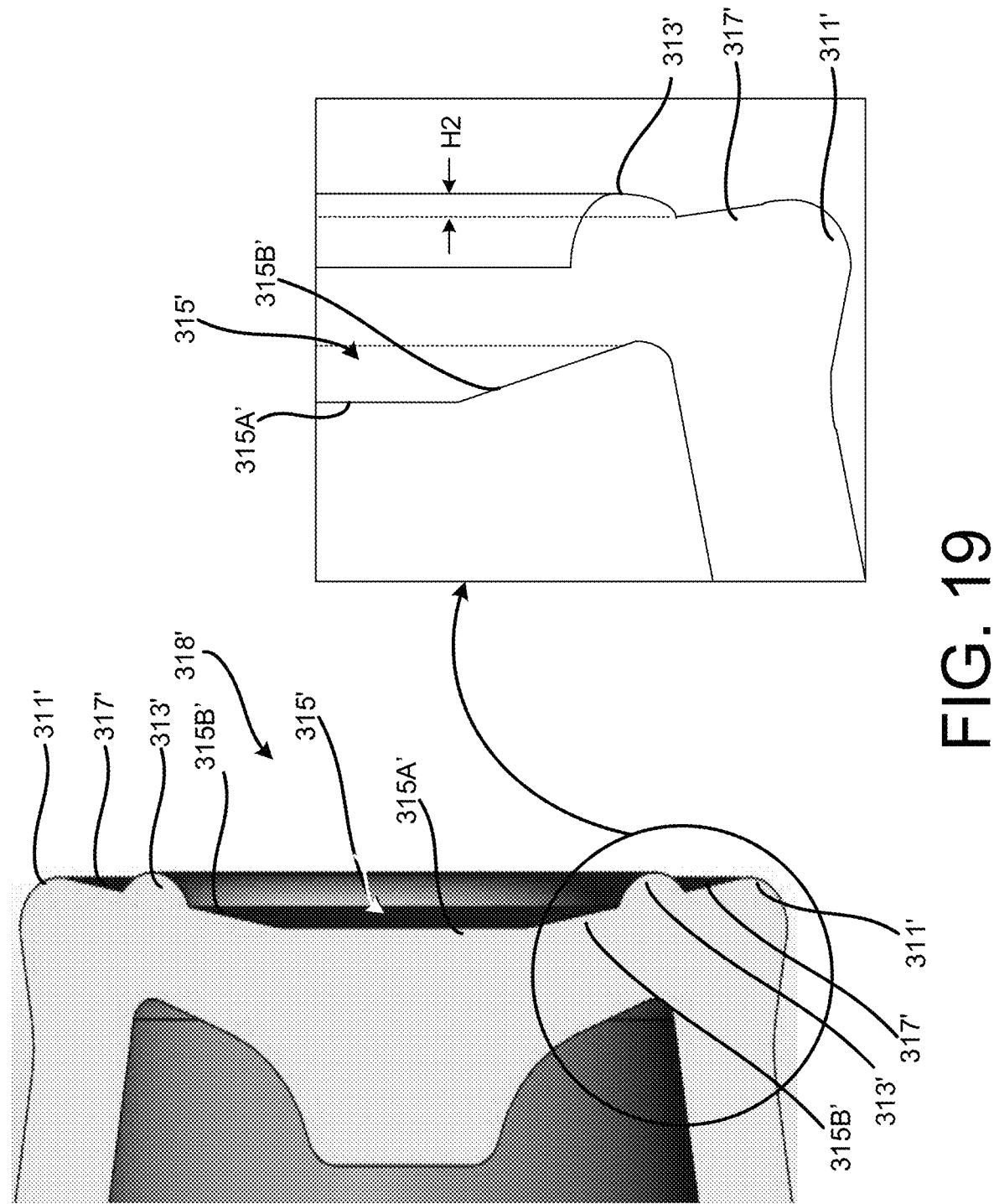
FIG. 19 is a cross-sectional view taken along line E-E of FIG. 18.

FIG. 16 is a perspective view of the button component 312, illustrating features of the button face 318, in accordance with an aspect. FIG. 17 is a cross-sectional view of the button component 312, taken along line D-D of FIG. 16. FIG. 18 is a perspective view of a button component 312', illustrating features of the button face 318', in accordance with another aspect. FIG. 19 is a cross-sectional view of the button component 312', taken along line E-E of FIG. 18.

In the example button component 312 shown in FIG. 16, and the example button component 312' shown in FIG. 18, the button face 318, 318' is substantially round, simply for purposes of discussion and illustration. The features of the button face 318, 318' to be described can be applied to button faces having other shapes.

In the example shown in FIGS. 16 and 17, the button face 318 includes an outer rim 311 defining an outer periphery of the button face 318. A raised ring 313 may be positioned on the button face 318, at an offset from the outer rim 311, for example, at an inner peripheral side of the outer rim 311. A contact area 315 may be defined within the raised rim 313. The raised ring 313 may protrude or extend beyond an outer face of the outer rim 311. For example, as shown in FIG. 17, the raised ring 313 may protrude beyond the outer face of the outer rim 311 by a distance H1. In some examples, the contact area 315 includes a central portion 315A and an inclined portion 315B extending between the central portion 315A and the raised ring 313.

In some examples, the protrusion of the raised ring 313 (i.e., by the distance H1 relative to the outer rim 311) may define a tactile feature that assists the user in locating the button face 318 for manipulation of the button component 312 and operation of the pump assembly 306 as described above. Similarly, the contour of the contact area 315 defined by the central portion 315A and the inclined portion 315B may guide the positioning of the finger of the user on the button component 312, to effectively manipulate the button component 312 for operation of the control valve 420/pump assembly 300 as described above. The raised ring 313 and the contour of the contact area 315 may facilitate location of the button component 312, may provide a contact area 315 that accommodates proper finger and/or thumb placement, and may enhance stability during user manipulation of the button component 312.

In the example shown in FIGS. 18 and 19, the example button component 312' has a button face 318' including an outer rim 311' defining an outer periphery of the button face 318'. A raised ring 313' may be positioned on the button face 318'. In the example shown in FIGS. 18 and 19, the raised ring 313' is spaced apart from the outer rim 311' by an intermediate surface 317'. The raised ring 313' may protrude or extend beyond an outer face of the outer rim 311'. For example, as shown in FIG. 19, the raised ring 313' may protrude beyond the outer face of the outer rim 311' by a distance H2. A contact area 315' may be defined within the raised rim 313'. In some examples, the contact area 315' includes a central portion 315A' and an inclined portion 315B' extending between the central portion 315A' and the raised ring 313'.

The protrusion of the raised ring 313' (i.e., by the distance H2 relative to the outer rim 311') may define a tactile feature that assists the user in locating the button face 318' for manipulation of the button component 312' and operation of the pump assembly 306 as described above. Similarly, the contour of the contact area 315' defined by the central portion 315A' and the inclined portion 315B' may guide the positioning of the finger of the user on the button component 312', to effectively manipulate the button component 312' for operation of the control valve 420/pump assembly 300 as described above. The raised ring 313' and the contour of the contact area 315' may facilitate location of the button component 312', may provide a contact area 315' that accommodates proper finger and/or thumb placement, and may enhance stability during user manipulation of the button component 312'.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:
1. An inflatable penile prosthesis, comprising:
a fluid reservoir configured to hold fluid;
an inflatable member; and
a pump assembly configured to transfer the fluid between the fluid reservoir and the inflatable member, the pump assembly including:
 a valve assembly, including:
  a housing:
  a valve block received in the housing; and
  a control valve positioned within a fluid passageway formed in the valve block and configured to move between an inflation position corresponding to an inflation mode of the pump assembly and a defla- tion position corresponding to a deflation mode of the pump assembly, the at least one valve including:
  a first movable member received in the fluid passageway, the first movable member including a valve body having a cavity defined therein, a flange extending outward from a portion of the valve body, and an opening at an end portion of the valve body defining an opening into the cavity;
  a second movable member having a head portion coupled to the housing and a shaft portion coupled to the head portion and movably received in the cavity defined in the valve body;
  a pump bulb coupled to a first portion of the valve assembly; and
  a plurality of fluid ports at a second portion of the valve assembly, including a first port fluidically connected to the fluid reservoir and a second port fluidically connected to the inflatable member,
wherein in the deflation position of the control valve, the flange is configured to engage a first lip defined in a wall portion of the fluid passageway and in the inflation position of the control valve, the flange is configured to engage a second lip defined in the wall portion of the fluid passageway.

2. The inflatable penile prosthesis of claim 1, wherein the control valve also includes a biasing member, the biasing member having an end that abuts the flange so as to apply a biasing force that biases the valve body against the first lip in the deflation position, and against the second lip in the inflation position.

3. The inflatable penile prosthesis of claim 1, wherein the control valve is configured to disengage the second lip and engage the first lip in response to an external force applied to the second movable member, to switch from the inflation mode to the deflation mode of the pump assembly.

4. The inflatable penile prosthesis of claim 1, further comprising a pressure relief channel defined in the wall portion of the fluid passageway, adjacent to the second lip, wherein the pressure relief channel is configured to shift the flange back into engagement with the second lip in response to a pressure in the fluid passageway that is greater than a threshold pressure.

5. The inflatable penile prosthesis of claim 1, wherein a length of the shaft portion is greater than a depth of the cavity.

6. The inflatable penile prosthesis of claim 1, wherein the shaft portion is tapered such that a diameter of the shaft portion at a proximal end portion of the second movable member is greater than a diameter of the shaft portion at a distal end portion of the second movable member.

7. The inflatable penile prosthesis of claim 1, wherein the shaft portion of the second movable member is received through an opening in a portion of the housing defining a button component of the pump assembly, such that the head portion is positioned at an outer side of the housing and the shaft portion is positioned at an interior side of the housing.

8. The inflatable penile prosthesis of claim 1, wherein the head portion of the second movable member is over molded by a material of a portion of the housing defining a button component of the pump assembly to couple the second movable member to the housing.

9. The inflatable penile prosthesis of claim 1, further comprising
  a refill valve controlling fluid flow from the reservoir to the pump bulb;
  an inflation valve controlling fluid flow from the pump bulb to the inflatable member; and
  an anti-auto inflation valve controlling a fluid flow between the inflatable member and the reservoir.

10. The inflatable penile prosthesis of claim 9, wherein the anti-auto inflation valve is a one-way valve that selectively allows a flow of fluid from the inflatable member to the reservoir, bypassing the pump bulb, and that restricts a flow of fluid from the reservoir to the inflatable member.

11. The inflatable penile prosthesis of claim 9, wherein the refill valve includes:
  a refill valve body;
  a protrusion at an intermediate portion of the refill valve body; and
  at least one groove formed in an outer peripheral portion of the protrusion on the refill valve body, extending in a flow direction of fluid through the refill valve; and
the inflation valve includes:
  an inflation valve body;
  a protrusion at an intermediate portion of the inflation valve body;
  at least one groove formed in an outer peripheral portion of the protrusion on the inflation valve body, extending in a flow direction of fluid through the inflation valve; and
  a biasing member having an end thereof positioned against the protrusion of the inflation valve body.

12. The inflatable penile prosthesis of claim 9, wherein portions of the fluid passageway include fluting to guide flow through the fluid passageway.

13. The inflatable penile prosthesis of claim 1, wherein the housing includes:
  a first housing;
  a second housing coupled to the first housing;
  at least one adhesive port defined in one of the first housing or the second housing; and
  at least one fill channel defined between mating surfaces of the first housing and the second housing, the at least one fill channel being fluidically connected to the at least one adhesive port such that adhesive injected into the at least one fill channel via the at least one adhesive port couples the first housing and the second housing.

14. An inflatable penile prosthesis, comprising:
  a fluid reservoir configured to hold fluid;
  an inflatable member; and
  a pump assembly operatively coupled to the fluid reservoir and the inflatable member, the pump assembly including:
    a valve assembly, including:
      a housing:
      a valve block received in the housing; and
      at least one valve positioned within a fluid passageway formed in the valve block and configured to move between an inflation position corresponding to an inflation mode of the pump assembly and a deflation position corresponding to a deflation mode of the pump assembly, the at least one valve including
    a first movable member received in the fluid passageway and a second movable member;
    a pump bulb coupled to a first portion of the valve assembly; and
    a plurality of fluid ports at a second portion of the valve assembly, including a first port fluidically connected to the fluid reservoir and a second port fluidically connected to the inflatable member, wherein the second movable member includes a head portion coupled to a portion of the housing and a shaft portion, the first movable member has a valve body defining a cavity therein, a flange extending outward from the valve body, and an end portion defining an opening into the cavity, the opening of the first movable member being configured to receive the shaft portion of the second movable member, wherein in the deflation position of the at least one valve, the flange is configured to engage a first lip defined in a wall portion of the fluid passageway, and in the inflation position of the at least one valve, the flange is configured to engage a second lip defined in the wall portion of the fluid passageway.

15. The inflatable penile prosthesis of claim 14, wherein the at least one valve also includes a biasing member, the biasing member having an end that abuts the flange so as to apply a biasing force that biases the valve body against the first lip in the deflation position, and against the second lip in the inflation position.

16. The inflatable penile prosthesis of claim 14, wherein the at least one valve is configured to disengage the second lip and engage the first lip in response to an external force applied to the second movable member, to switch from the inflation mode to the deflation mode of the pump assembly.

17. The inflatable penile prosthesis of claim 14, wherein the at least one valve is a control valve, the penile prosthesis further comprising:
- a refill valve controlling fluid flow from the reservoir to the pump bulb;
- an inflation valve controlling fluid flow from the pump bulb to the inflatable member; and
- an anti-auto inflation valve controlling a fluid flow between the inflatable member and the reservoir.

18. The inflatable penile prosthesis of claim 17, wherein the anti-auto inflation valve is a one-way valve that selectively allows a flow of fluid from the inflatable member to the reservoir, bypassing the pump bulb, and that restricts a flow of fluid from the reservoir to the inflatable member.

* * * * *